US012589069B2

(12) United States Patent
Shawer et al.

(10) Patent No.: US 12,589,069 B2
(45) Date of Patent: ***Mar. 31, 2026

(54) OPHTHALMIC SUSPENSION COMPOSITION

(71) Applicant: Bausch + Lomb Ireland Limited, Dublin (IE)

(72) Inventors: Mohannad Shawer, Lexington, MA (US); Eric Phillips, Ontario, NY (US); Martin J. Coffey, Buffalo Grove, IL (US)

(73) Assignee: Bausch + Lomb Ireland Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/086,286

(22) Filed: Dec. 21, 2022

(65) Prior Publication Data

US 2023/0140895 A1 May 11, 2023

Related U.S. Application Data

(63) Continuation of application No. 16/826,366, filed on Mar. 23, 2020, now Pat. No. 11,534,395, which is a continuation of application No. 15/006,525, filed on Jan. 26, 2016, now Pat. No. 10,596,107.

(60) Provisional application No. 62/107,696, filed on Jan. 26, 2015.

(51) Int. Cl.

| | |
|---|---|
| *A61K 9/00* | (2006.01) |
| *A61K 9/14* | (2006.01) |
| *A61K 31/56* | (2006.01) |
| *A61K 31/573* | (2006.01) |
| *A61K 47/02* | (2006.01) |
| *A61K 47/06* | (2006.01) |
| *A61K 47/10* | (2017.01) |
| *A61K 47/32* | (2006.01) |
| *A61K 47/38* | (2006.01) |
| *A61P 27/02* | (2006.01) |

(52) U.S. Cl.
CPC .............. *A61K 9/0048* (2013.01); *A61K 9/14* (2013.01); *A61K 9/146* (2013.01); *A61K 31/56* (2013.01); *A61K 31/573* (2013.01); *A61K 47/02* (2013.01); *A61K 47/06* (2013.01); *A61K 47/10* (2013.01); *A61K 47/32* (2013.01); *A61K 47/38* (2013.01); *A61P 27/02* (2018.01)

(58) Field of Classification Search
CPC ...... A61K 31/56; A61K 31/573; A61K 47/02; A61K 47/06; A61K 47/10; A61K 47/32; A61K 47/38; A61K 9/0048; A61K 9/14; A61K 9/146; A61P 27/02
See application file for complete search history.

(56) References Cited

U.S. PATENT DOCUMENTS

| | | | |
|---|---|---|---|
| 4,540,930 A | 9/1985 | Siedband | |
| 4,615,697 A | 10/1986 | Robinson | |
| 4,996,335 A | 2/1991 | Bodor | |
| 5,192,535 A | 3/1993 | Davis et al. | |
| 5,252,318 A | 10/1993 | Joshi et al. | |
| 5,427,778 A | 6/1995 | Finkenaur et al. | |
| 5,538,721 A | 7/1996 | Babcock et al. | |
| 5,556,848 A | 9/1996 | Kimura et al. | |
| 6,511,660 B1 | 1/2003 | Lin et al. | |
| 7,001,615 B1 | 2/2006 | Singh et al. | |
| 7,834,059 B2 | 11/2010 | Wong | |
| 7,919,483 B2 | 4/2011 | Wortzman et al. | |
| 8,071,648 B2 | 12/2011 | Wong | |
| 8,324,281 B2 | 12/2012 | Wong | |
| 8,921,337 B2 | 12/2014 | Chowhan et al. | |
| 9,827,191 B2 | 11/2017 | Popov et al. | |
| 11,534,395 B2 * | 12/2022 | Shawer .................. | A61K 9/146 |
| 2002/0187998 A1 | 12/2002 | Ueno | |
| 2005/0182039 A1 | 8/2005 | Meyering | |
| 2006/0122277 A1 | 6/2006 | Wong | |
| 2007/0110812 A1 | 5/2007 | Xia et al. | |
| 2010/0004225 A1 | 1/2010 | Lichter et al. | |
| 2010/0226997 A1 | 9/2010 | Bowman et al. | |
| 2010/0234336 A1 | 9/2010 | Xia et al. | |
| 2011/0015271 A1 | 1/2011 | Wong | |
| 2012/0028947 A1 | 2/2012 | Xia et al. | |
| 2013/0079315 A1 | 3/2013 | Coffey | |
| 2013/0303502 A1 | 11/2013 | Cavanagh et al. | |
| 2014/0328917 A1 | 11/2014 | Tada et al. | |
| 2015/0202306 A1 | 7/2015 | Coffey | |

FOREIGN PATENT DOCUMENTS

| | | |
|---|---|---|
| AU | 2015288643 B2 | 1/2016 |
| AU | 2015288644 B2 | 1/2016 |

(Continued)

OTHER PUBLICATIONS

Goodwin et al.; Carbohydrate Polymers; 83; pp. 843-851. Published Sep. 29, 2010.*
Ali et al., "Undustrial perspective in ocular drug delivery", Advanced Drug Delivery Reviewed, 58 (2006), pp. 1258-1268.
Alrex™ (1998) "loteprednol etabonate ophthalmic suspension," Bausch & Lomb Pharmaceuticals, Inc., 13 pages.
Andonova et al., "Eye Drops with nanoparticles as Drug Delivery Systems", International Journal of Pharmacy and Pharmaceutical Sciences, vol. 7, Issue 2, Issn 0975-1491, 2015 (5 pages).

(Continued)

*Primary Examiner* — Jeffrey T. Palenik
(74) *Attorney, Agent, or Firm* — McNeill PLLC

(57) ABSTRACT

A suspension includes an ophthalmic active ingredient suspended in a formulation vehicle including a suspending agent and a non-ionic cellulose derivative. The ophthalmic active agent is present as particles having $D_{v90}<5$ μm and $D_{v50}<1$ μm. The suspension may be administered to a patient for treating an ophthalmic inflammatory condition.

20 Claims, 38 Drawing Sheets

(56)                 References Cited

FOREIGN PATENT DOCUMENTS

| CN | 101966143 A | 2/2011 |
|---|---|---|
| CN | 104602670 A | 5/2015 |
| EP | 0663208 A2 | 7/1995 |
| EP | 0659433 A1 | 6/2001 |
| EP | 2586426 A1 | 5/2013 |
| EP | 3250185 B1 | 12/2018 |
| IN | 2437/MUM/2014 | 10/2015 |
| JP | 2015526515 A | 9/2015 |
| KR | 20140069210 A | 6/2014 |
| WO | 1989006964 A1 | 8/1989 |
| WO | 2004006959 A1 | 1/2004 |
| WO | 2004112836 A2 | 12/2004 |
| WO | 2006083840 A1 | 8/2006 |
| WO | 2007058935 A1 | 5/2007 |
| WO | 2013043387 A1 | 3/2013 |
| WO | 2013166385 A1 | 11/2013 |
| WO | 2013166436 A1 | 11/2013 |
| WO | 2013169458 A1 | 11/2013 |
| WO | 2013169647 A1 | 11/2013 |
| WO | 2014035450 A1 | 3/2014 |
| WO | 2014035451 A1 | 3/2014 |
| WO | 2015105652 A1 | 7/2015 |
| WO | 2016006701 A1 | 1/2016 |
| WO | 2016006702 A1 | 1/2016 |
| WO | 2016016908 A1 | 2/2016 |
| WO | 2016123079 A1 | 8/2016 |

OTHER PUBLICATIONS

Bausch & Lomb Incorporated (2014) "NCT02208297, Loteprednol Ophthalmic Gel for the Treatment of Ocular Inflammation and Pain Following Cataract Surgery" National Library of Medicine, 12 pages.

Bausch & Lomb Incorporated (2014) "NCT01996839, Loteprednol Ophthalmic Gel for the Treatment of Ocular Inflammation and Pain Following Cataract Surgery" National Library of Medicine, 12 pages.

Cavet et al., "Ocular pharmacokinetics of submicron loteprednol etabonate ophthalmic gel, 0.38% following topical administration in rabbits", Investigative Ophthalmology & Visual Science, Jun. 2015, vol. 56, 1524 (2 pages).

Coffey et al., "Development of a non-settling gel formulation of 0.5% loteprednol etabonate for anti-inflammatory useas an ophthalmic drop", Clinical Ophthalmology, Dove Medical Press Ltd., 2013 (14 pages).

Huichao et al., "The application of biomedical polymer material hydroxy propyl methyl cellulose(HPMC) in pharmaceutical preparations", Journal of Chemical and Pharmaceutical Research, ISSN 0975-7384, 2014 (6 pages).

International Search Report and Written Opinion for PCT/US2016/014872 of the International Searching Authority, 10 pages, Apr. 11, 2016.

Jothi et al., "In-Situ Ophthalmic Gels for the Treatment of Eye Diseases", UUPSR, 2012; vol. 3(7); 1891-1904.

Kassem et al., "Nanosuspension as an ophthalmic delivery system for certain glucocorticoid drugs", International Journal of Pharmaceutics, Mar. 2007, 340:126-133.

Khangtragool, A., "Methocel E4M: Preparation and Properties as a Vehicle for the Ocular Drug Delivery of Vancomycin", Chiang Mai Journal of Science, Feb. 2014, 41(1): 166-173.

Kumar et al., "In situ-forming gels for ophthalmic drug delivery" J. Ocular Pharmacol, vol. 10, 47-56 (1994).

Kumar et al., "Modification of in situ gelling behavior of carbopol solutions by hydroxypropyl methylcellulose" J. Pharm. Sci., vol. 84, 344-348 (1995).

Lakshmi et al., "Nano-suspension Technology: A Review", International Journal of Pharmacy and Pharmaceutical Sciences, ISSN 0975-1491, 2010 (6 pages).

Liu et al., "Nanosuspensions of poorly soluble drugs: preparation and development by wet milling" Int. J. of Pharm., 411(1-2):215-222, 2011.

Lotemax™ (1998) "loteprednol etabonate ophthalmic suspension, 0.5%" Bausch & Lomb Pharmaceuticals, Inc., 16 pages.

Lotemax™ (2012) "loteprednol etabonate ophthalmic gel" Bausch & Lomb Incorporated, 4 pages.

Memon et al., "Optimization of Formulation Parameters on Ocular Loteprednol Etabobate Nanosuspension by Media Milling Method" International Journal of Pharmaceutical & Biological Archives, ISSN 0976-3333, 2013 (6 pages).

Modern Medicine Feature Articles: "Results Positive for B+L sub-micron gel formulation of loteprednol etabonate" Ophthalmology Times, 2014 (3 pages).

Nagai et al., "A New Preparation Method for Ophthalmic Drug Nanoparticles" Pharmaceutica Analytica Acta, ISSN 20153-2435 PAA, 2014 (4 pages).

Nagai et al., "Therapeutic Effects of Gel Ointments Containing Tranilast Nanoparticles on Paw Edema in Adjuvant-Induced Arthritis Rats" Biol. Pharm. Bull. 37(1) 96-104, vol. 37 No. 1, 2014 (9 pages).

Notice of Opposition to a European Patent filed in corresponding European Application No. 16704744.8 filed by Allergan, Inc. on Sep. 4, 2019 (5 pages).

Notice of Opposition to a European Patent filed in corresponding European Application No. 16704744.8 filed by Dr. Markus Breuer on Sep. 5, 2019 (4 pages).

Notice of Opposition to a European Patent filed in corresponding European Application No. 16704744.8 filed by European Oppositions Limited on Sep. 5, 2019 (6 pages).

Ogawa et al., "Topical tranilast for treatment of the early stage of mild dry eye associated with chronic GVHD", Bone Marrow Transplantation, Macmillan Publishers Limited, 2010 (5 pages).

Pawar et al., "Engineered nanocrystal technology: In-vivo fate, targeting and applications in drug delivery", Journal of Controlled Release, Aug. 2013, 183:51-66.

Peltonen et al., "Drug Nanocrystals and Nanosuspensions in Medicine", Handbook of Nanobiomedical Research, Sep. 2014, vol. 1, 169-197.

Rajoria et al., "In-Situ Gelling System: A Novel Approach for Ocular Drug Delivery", American Journal of Pharmtech Research, ISSN 2249-3387, 2012 (30 pages).

Rowe, Raymond C., "Carbomer" Handbook of Pharmaceutical Excipients, vol. 5, 2005 (5 pages).

Rowe, Raymond C., "Carboxymethylcellulose Sodium" Handbook of Pharmaceutical Excipients, 2005 (4 pages).

Rowe, Raymond C., "Hypromellose" Handbook of Pharmaceutical Excipients, vol. 5, 2005 (4 pages).

Rowe, Raymond C., "Methycellulose" Handbook of Pharmaceutical Excipients, vol. 5, 2005 (4 pages).

Rozier et al., "GelriteÒ: A novel, ion-activated, in-situ gelling polymer for ophthalmic vehicles. Effect on bioavailability of timolol" International Journal of Pharmaceutics (1989), 57: 163-168.

Schoenwald et al., "Ophthalmic bioequivalence of steroid/antibiotic combination formulations" Biopharm Drug Dispos. 1987; 8:527-548.

Schopf et al., "Ocular Pharmacokinetics of a Novel Loteprednol Etabonate 0.4% Opthalmic Formulation" Opthalmology and Therapy, 3 (2014), pp. 63-72.

Tang et al., "The effect of azone on ocular levobunolol absorption: calculating the area under the curve and its standard error using tissue sampling compartments" Pharm Res. 1988; 5:238-241.

Van Eerdenbrugh et al., "A Screening Study of Surface Stabilization during the Production of Drug Nanocrystals", Journal of Pharmaceutical Sciences, vol. 98, No. 6, pp. 2091-2103, Jun. 2009 (13 pages).

Wang et al., "Stability of nanosuspensions in drug delivery", Journal of Controlled Release, Aug. 2013, 172:1126-1141.

* cited by examiner

FIGURE 3

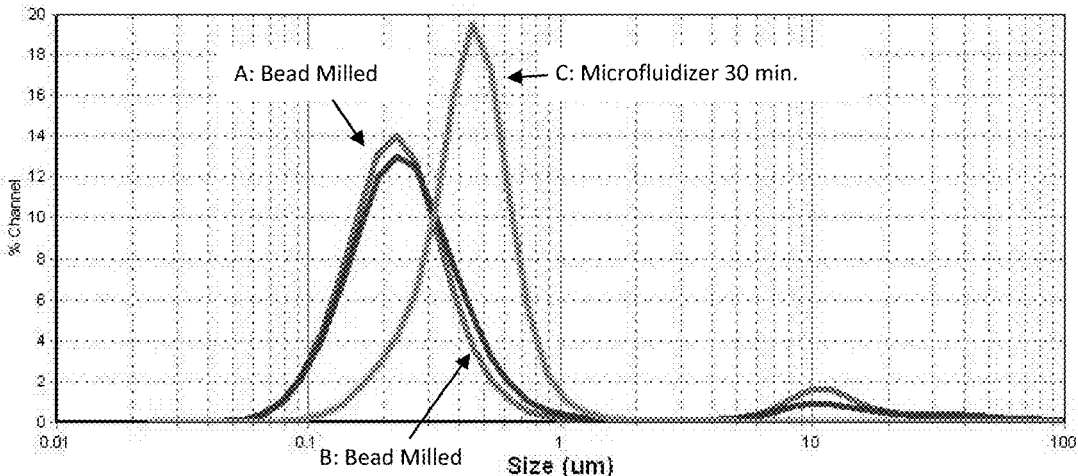

A= DB: 218:30% LE, Poloxamer/BAK:direct addition
B= DB: 223:30% LE, Poloxamer:direct addition
C= DB: 260:3026-MJC-163F, Poloxamer/BAK: 180 min at 25K psi

FIGURE 4

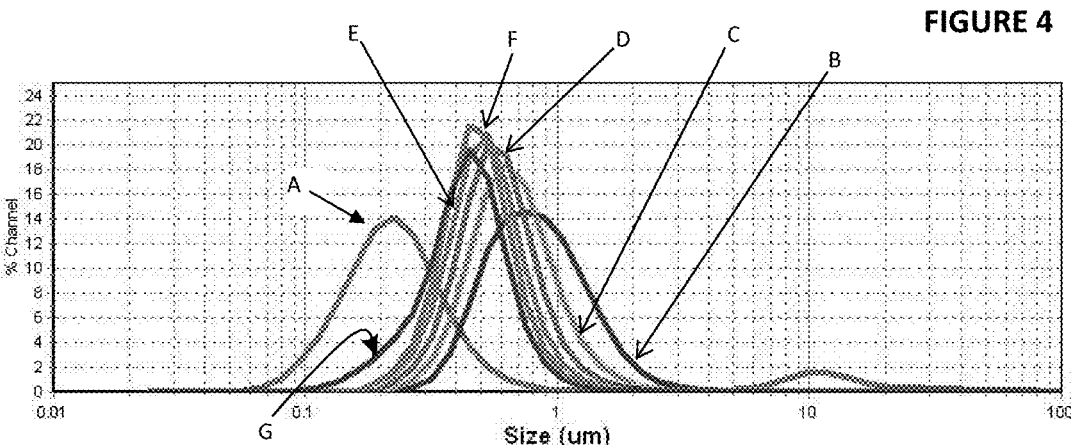

A= DB: 218:30% LE, Poloxamer/BAK:direct addition
B= DB: 233:3026-MJC-163A, Poloxamer/BAK:30 min at 25K psi, 215.4 mg
C= DB 238:3026-MJC-163B, Poloxamer/BAK:60 min at 25K psi
D= DB: 243:3026-MJC-163C, Poloxamer/BAK:90 min at 25K psi
E= DB: 250:3026-MJC-163D, Poloxamer/BAK:120 min at 25K psi
F= DB: 255:3026-MJC-163E, Poloxamer/BAK:150 min at 25K psi
G= DB: 260:3026-MJC-163F, Poloxamer/BAK:180 min at 25K psi A= DB: 327:3026-MJC-164A 2.0 mm beads:20% LE/8% F127 direct add
B= DB: 338:3026-MJC-164B 1.0 mm beads:20% LE/2% F127 direct add
C= DB: 349:3026-MJC-164C 0.5 mm beads:20% LE/2% F127 direct add
D= DB: 360:3026-MJC-165C:22%LE/2.2% F127/0.22%BAK -
E= DB: 371:3026-MJC-165B:22%LE/2.2% F127/0.22%BAK
F= DB: 382:3026-MJC-165A:20%LE/2.2% F127/0.22%BAK A= DB: 426:1 .55 pol/30% LE: 3026-MJC-166A 20:1
B= DB: 492:3604-MJC-167A:30% LE/1.0% Polox 30:1
C= DB: 503.3023-MJC-167B:30% LE/0.75% Polox 40:1
D= DB: 525:1.5% Polox / 30% LE: 3026-MJC-166A-2 (milled more)
E= DB: 536:1.0% Polox / 30% LE: 3026-MJC-167A-2 (milled more)
F= DB: 547:0.75% Polox / 30% LE: 3026-MJC-167B-2 (milled more)

Tear Fluid

Tear Fluid

Bulbar Conjunctiva

Bulbar Conjunctiva

Cornea

Cornea

Aqueous Humor

BLQ Footnote:
0.38% LE with Submicron Particles - 13 Samples ('X' symbols)
0.38% LE with Small-Sized Particles - 17 Samples ('+' symbols)
0.75% LE with Unmodified Particles – 7 Samples ('-' symbols)
Lotemax Gel – 8 Samples ('*' symbols)

Aqueous Humor

Iris/Ciliary Body

Iris/Ciliary Body

Tear Fluid

* - Statistically significant (p ≤0.05) from Lotemax Gel

Bulbar Conjunctiva

* – Statistically significant (p ≤ 0.05) from Lotemax Gel

Cornea

* - Statistically significant (p ≤0.05) from Lotemax Gel

Aqueous Humor

* - Statistically significant (p ≤0.05) from Lotemax Gel

Iris/Ciliary Body

Figure 26

Tear Fluid

| Time (h) | Rabbit 1 (OD) | Rabbit 1 (OS) | Rabbit 2 (OD) | Rabbit 2 (OS) | Rabbit 3 (OD) | Rabbit 3 (OS) | Mean | SD | CV% |
|---|---|---|---|---|---|---|---|---|---|
| Group 1: 0.38% Submicron Formulation | | | | | | | | | |
| 0.0833 | 1730 | 1220 | 135 | 132 | 328 | 136 | 614 | 691 | 113 |
| 0.25 | 24.0 | 652 | 15.1 | 506 | 97.9 | 69.4 | 227 | 278 | 122 |
| 0.5 | 143 | 18.8 | 2.79 | 47.7 | 13.4 | 8.04 | 39.0 | 53.3 | 137 |
| 1 | 8.41 | 13.9 | 116 | 56.5 | 10.7 | 20.5 | 37.7 | 42.3 | 112 |
| 2 | 1.26 | 1.88 | 2.49 | 37.7[a] | 0.834 | 8.76 | 3.04 | 3.26 | 107 |
| 4 | 0.482 | 6.2[a] | 0.543 | 40.6[a] | 0.561 | 0.123 | 0.427 | 0.206 | 48 |
| 8 | 0.104 | 5.74 | 0.0654 | 44.9[a] | 0.515 | 3.86 | 2.06 | 2.60 | 126 |
| 12 | 0.0275 | 1.64 | 6.07 | 15.5 | 0.877 | 2.49 | 4.43 | 5.81 | 131 |
| 24 | 0.0464 | 0.380 | 0.0370 | 0.521 | 0.00625[a] | 0.179 | 0.233 | 0.213 | 91 |
| Group 2: 0.38% Micronized Formulation | | | | | | | | | |
| 0.0833 | 76.1 | 162 | 83.7 | 39.4 | 101 | 744 | 201 | 269 | 134 |
| 0.25 | 155 | 52.6 | 129 | 29.0 | 64.5 | 113 | 90.5 | 49.1 | 54 |
| 0.5 | 2.59 | 667[a] | 19.6 | 27.6 | 48.0 | 10.2 | 21.6 | 17.5 | 81 |
| 1 | 29.7 | 14.5 | 1.05 | 9.70 | 12.9 | 142[a] | 13.6 | 10.4 | 76 |
| 2 | 27.6 | 4.88 | 1.72 | 10.1 | 3.15 | 3.99 | 8.57 | 9.75 | 114 |
| 4 | 24.0 | 18.7 | 2.62 | 4.53 | 2.62 | 7.24 | 9.95 | 9.14 | 92 |
| 8 | 22.5 | 6.02 | 0.435 | 0.800 | 0.0353 | 337[a] | 5.96 | 9.56 | 160 |
| 12 | 1.43 | 0.206 | 0.119 | 2.55 | 0.0201 | 2.55 | 1.15 | 1.20 | 104 |
| 24 | 0.998 | 1.36 | 0.0485 | 0.788 | 16.7[a] | 1.95 | 1.03 | 0.703 | 68 |

Figure 27

Tear Fluid

| Time (h) | Rabbit 1 (OD) | Rabbit 1 (OS) | Rabbit 2 (OD) | Rabbit 2 (OS) | Rabbit 3 (OD) | Rabbit 3 (OS) | Mean | SD | CV% |
|---|---|---|---|---|---|---|---|---|---|
| Group 3: 0.75% Unmodified Formulation | | | | | | | | | |
| 0.0833 | 547 | 956 | 225 | 174 | 161 | 46.0 | 352 | 341 | 97 |
| 0.25 | 61.5 | 2490 | 3860[a] | 387 | 250 | 175 | 673 | 1020 | 152 |
| 0.5 | 36.1 | 52.4 | 44.3 | 2.51 | 492[a] | 49.9 | 37.0 | 20.3 | 55 |
| 1 | 48.0 | 20.1 | 62.0 | 22.9 | 66.0 | 2.45 | 36.9 | 25.6 | 69 |
| 2 | 65.5 | 10.1 | 26.9 | 11.4 | 14.0 | 17.5 | 24.2 | 21.1 | 87 |
| 4 | 0.163 | 3.67 | 10.9 | 37.2 | 1.05 | 13.5 | 11.1 | 13.9 | 125 |
| 8 | 2.17 | 26.9 | 2.29 | 4.21 | 12.9 | 12.2 | 10.1 | 9.52 | 94 |
| 12 | 0.388 | 16.0[a] | 0.964 | 1.21 | 1.65 | 6.61 | 2.16 | 2.53 | 117 |
| 24 | 8.50 | 5.06 | 1.34 | 0.254 | 1.72 | 3.79 | 3.44 | 3.03 | 88 |
| Group 4: 0.5% Lotemax Gel | | | | | | | | | |
| 0.0833 | 130 | 689 | 1090 | 291 | 290 | 280 | 462 | 360 | 78 |
| 0.25 | 1160 | 107 | 1670 | 2200 | 8.42 | 83.3 | 871 | 942 | 108 |
| 0.5 | 4.34 | 41.2 | 324 | 73.5 | 29.9 | 76.4 | 91.6 | 117 | 128 |
| 1 | 113 | 14.4 | 3750[a] | 4.21 | 6.22 | 91.6 | 45.9 | 52.2 | 114 |
| 2 | 0.129 | 30.8 | 1.61 | 254[a] | 12.0 | 76.6 | 24.2 | 31.7 | 131 |
| 4 | 8.32 | 6.72 | 3.48 | 128[a] | 46.9 | 1.28 | 13.3 | 19.0 | 143 |
| 8 | 0.491 | 48.2[a] | 1.84 | 4.98 | 0.266 | 57.1[a] | 1.89 | 2.17 | 115 |
| 12 | 14.9 | 1.96 | 16.9 | 1.26 | 1.43 | 19.8 | 9.38 | 8.72 | 93 |
| 24 | 0.237 | 0.388 | 0.0133 | 0.528 | 0.141 | 1.14 | 0.408 | 0.402 | 99 |

Figure 28

Bulbar Conjunctiva

| Time (h) | Rabbit 1 (OD) | Rabbit 1 (OS) | Rabbit 2 (OD) | Rabbit 2 (OS) | Rabbit 3 (OD) | Rabbit 3 (OS) | Mean | SD | CV% |
|---|---|---|---|---|---|---|---|---|---|
| Group 1: 0.38% Submicron Formulation | | | | | | | | | |
| 0.0833 | 13.7 | 10.1 | 36.4 | 3.46 | 1.77 | 6.40 | 12.0 | 12.7 | 106 |
| 0.25 | 8.23 | 6.02 | 9.01 | 3.54 | 14.2 | 7.45 | 8.08 | 3.57 | 44 |
| 0.5 | 1.56 | 2.22 | 3.04 | 6.53 | 3.10 | 2.31 | 3.13 | 1.76 | 56 |
| 1 | 2.51 | 3.77 | 12.5 | 5.00 | 2.40 | 2.01 | 4.70 | 3.98 | 85 |
| 2 | 8.00 | 1.83 | 3.14 | 1.81 | 3.95 | 3.09 | 3.64 | 2.29 | 63 |
| 4 | 1.13 | 0.792 | 1.01 | 4.23 | 0.239 | 2.07 | 1.58 | 1.43 | 91 |
| 8 | 0.0897 | 1.22 | 0.549 | 1.59 | 0.646 | 0.427 | 0.754 | 0.551 | 73 |
| 12 | 2.55 | 0.549 | 2.13 | 2.26 | 0.226 | 0.940 | 1.44 | 0.990 | 69 |
| 24 | 0.394 | 0.196 | 0.0283 | 0.131 | 0.0952 | 0.0723 | 0.153 | 0.131 | 86 |
| Group 2: 0.38% Micronized Formulation | | | | | | | | | |
| 0.0833 | 9.97 | 12.7 | 6.71 | 64.5 | 6.35 | 23.2 | 20.6 | 22.4 | 109 |
| 0.25 | 259 | 16.7 | 7.11 | 142 | 40.3 | 6.96 | 78.7 | 102 | 130 |
| 0.5 | 2.26 | 4.05 | 13.6 | 7.96 | 7.37 | 8.23 | 7.25 | 3.92 | 54 |
| 1 | 11.0 | 11.1 | 0.607 | 1.20 | 0.477 | 2.65 | 4.51 | 5.13 | 114 |
| 2 | 2.04 | 32.4[a] | 1.04 | 2.06 | 5.97 | 1.58 | 2.54 | 1.96 | 77 |
| 4 | 3.35 | 9.67 | 0.814 | 0.739 | 4.51 | 1.84 | 3.49 | 3.37 | 97 |
| 8 | 4.96 | 0.944 | 0.536 | 1.03 | 0.342 | 0.274 | 1.35 | 1.80 | 133 |
| 12 | 0.597 | 0.475 | 0.237 | 0.223 | 0.963 | 0.662 | 0.526 | 0.280 | 53 |
| 24 | 0.217 | 2.62 | 0.0619 | 0.676 | 0.821 | 1.61 | 1.00 | 0.962 | 96 |

Figure 29

Bulbar Conjunctiva

| Time (h) | Rabbit 1 (OD) | Rabbit 1 (OS) | Rabbit 2 (OD) | Rabbit 2 (OS) | Rabbit 3 (OD) | Rabbit 3 (OS) | Mean | SD | CV% |
|---|---|---|---|---|---|---|---|---|---|
| Group 3: 0.75% Unmodified Formulation | | | | | | | | | |
| 0.0833 | 12.1 | 9.66 | 5.99 | 3.59 | 3.12 | 8.17 | 7.11 | 3.52 | 50 |
| 0.25 | 84.5 | 9.15 | 8.21 | 22.0 | 4.93 | 5.71 | 22.4 | 31.0 | 138 |
| 0.5 | 2.83 | 3.88 | 2.78 | 2.81 | 5.27 | 3.70 | 3.55 | 0.975 | 27 |
| 1 | 12.4 | 10.5 | 9.99 | 5.02 | 5.91 | 3.74 | 7.93 | 3.49 | 44 |
| 2 | 6.45 | 16.5 | 6.00 | 5.77 | 0.819 | 3.71 | 6.54 | 5.31 | 81 |
| 4 | 37.1 | 1.80 | 9.21 | 3.71 | 8.34 | 4.90 | 10.8 | 13.2 | 122 |
| 8 | 10.8 | 5.32 | 2.48 | 2.29 | 7.44 | 4.64 | 5.50 | 3.23 | 59 |
| 12 | 0.323 | 2.12 | 2.16 | 1.13 | 0.983 | 0.571 | 1.21 | 0.772 | 64 |
| 24 | 1.61 | 0.477 | 2.42 | 0.471 | 1.46 | 3.48 | 1.65 | 1.16 | 70 |
| Group 4: 0.5% Lotemax Gel | | | | | | | | | |
| 0.0833 | 33.8 | 4.83 | 12.6 | 7.40 | 14.2 | 7.02 | 13.3 | 10.7 | 80 |
| 0.25 | 9.05 | 2.07 | 15.6 | 55.6 | 7.76 | 8.57 | 16.4 | 19.7 | 120 |
| 0.5 | 5.65 | 6.06 | 9.27 | 8.86 | 14.5 | 9.23 | 8.93 | 3.17 | 35 |
| 1 | 287[a] | 12.2 | 6.61 | 4.81 | 8.76 | 13.6 | 9.20 | 3.69 | 40 |
| 2 | 0.831 | 74.9[a] | 2.36 | 0.719 | 8.55 | 4.07 | 3.31 | 3.23 | 98 |
| 4 | 4.98 | 5.19 | 12.0 | 11.2 | 4.32 | 6.47 | 7.36 | 3.37 | 46 |
| 8 | 6.10 | 2.03 | 6.37 | 0.994 | 5.51 | 1.84 | 3.81 | 2.44 | 64 |
| 12 | 1.43 | 5.98 | 0.757 | 0.714 | 4.35 | 12.9 | 4.36 | 4.70 | 108 |
| 24 | 0.477 | 0.199 | 0.121 | 0.554 | 0.388 | 0.779 | 0.420 | 0.241 | 57 |

Figure 30

Cornea

| Time (h) | Rabbit 1 (OD) | Rabbit 1 (OS) | Rabbit 2 (OD) | Rabbit 2 (OS) | Rabbit 3 (OD) | Rabbit 3 (OS) | Mean | SD | CV% |
|---|---|---|---|---|---|---|---|---|---|
| Group 1: 0.38% Submicron Formulation | | | | | | | | | |
| 0.0833 | 3.38 | 2.06 | 5.07 | 4.09 | 5.09 | 2.73 | 3.74 | 1.24 | 33 |
| 0.25 | 2.13 | 2.01 | 2.06 | 1.74 | 2.74 | 2.13 | 2.14 | 0.330 | 15 |
| 0.5 | 0.590 | 0.795 | 0.935 | 1.28 | 2.28 | 1.65 | 1.26 | 0.627 | 50 |
| 1 | 1.07 | 0.709 | 0.715 | 0.940 | 1.940 | 0.705 | 1.010 | 0.478 | 47 |
| 2 | 0.668 | 0.324 | 0.563 | 0.572 | 1.572 | 0.246 | 0.658 | 0.476 | 72 |
| 4 | 0.251 | 0.506 | 0.152 | 0.534 | 1.534 | 0.229 | 0.534 | 0.514 | 96 |
| 8 | 0.0318 | 0.0662 | 0.0566 | 0.243 | 1.243 | 0.150 | 0.298 | 0.4690 | 157 |
| 12 | 0.151 | 0.194 | 0.345 | 0.606 | 1.606 | 0.150 | 0.509 | 0.565 | 111 |
| 24 | 0.0923 | 0.0648 | 0.463 | 0.0272 | 1.0272 | 0.0185 | 0.282 | 0.401 | 142 |
| Group 2: 0.38% Micronized Formulation | | | | | | | | | |
| 0.0833 | 0.962 | 1.17 | 2.07 | 1.94 | 2.94 | 1.67 | 1.79 | 0.708 | 40 |
| 0.25 | 3.27 | 2.50 | 3.23 | 0.700 | 1.700 | 2.16 | 2.26 | 0.98 | 43 |
| 0.5 | 0.500 | 0.645 | 1.16 | 1.22 | 2.22 | 0.331 | 1.010 | 0.691 | 68 |
| 1 | 0.198 | 0.341 | 0.256 | 0.259 | 1.259 | 0.307 | 0.437 | 0.4060 | 93 |
| 2 | 0.0498 | 0.243 | 0.139 | 0.0917 | 1.0917 | 0.205 | 0.303 | 0.3930 | 130 |
| 4 | 0.188 | 0.334 | 0.0378 | 0.0477 | 1.0477 | 0.535 | 0.365 | 0.383 | 105 |
| 8 | 0.0290 | 0.109 | 0.0644 | 0.0621 | 1.0621 | 0.0371 | 0.2270 | 0.4100 | 181 |
| 12 | 0.112 | 0.0709 | 0.0931 | 0.0594 | 1.0594 | 0.215 | 0.268 | 0.3920 | 146 |
| 24 | 0.0355 | 0.0869 | 0.00901 | 0.0688 | 1.0688 | 0.0438 | 0.2190 | 0.4170 | 190 |

Figure 31

Cornea

| Time (h) | Rabbit 1 (OD) | Rabbit 1 (OS) | Rabbit 2 (OD) | Rabbit 2 (OS) | Rabbit 3 (OD) | Rabbit 3 (OS) | Mean | SD | CV% |
|---|---|---|---|---|---|---|---|---|---|
| Group 3: 0.75% Unmodified Formulation | | | | | | | | | |
| 0.0833 | 2.39 | 3.96 | 1.73 | 1.69 | 2.69 | 4.21 | 2.78 | 1.09 | 39 |
| 0.25 | 2.54 | 1.45 | 3.15 | 1.37 | 2.37 | 0.972 | 1.98 | 0.837 | 42 |
| 0.5 | 0.335 | 0.624 | 1.22 | 0.469 | 1.469 | 1.28 | 0.900 | 0.480 | 53 |
| 1 | 0.724 | 0.431 | 0.500 | 0.433 | 1.433 | 0.640 | 0.694 | 0.381 | 55 |
| 2 | 1.94 | 0.788 | 0.462 | 0.418 | 1.418 | 0.235 | 0.877 | 0.667 | 76 |
| 4 | 0.163 | 0.183 | 2.20 | 1.51 | 2.51 | 0.161 | 1.120 | 1.090 | 97 |
| 8 | 0.181 | 0.236 | 0.150 | 0.199 | 1.199 | 0.114 | 0.347 | 0.4200 | 121 |
| 12 | 0.173 | 0.675 | 0.155 | 2.12$^a$ | 2.12$^a$ | 0.135 | 0.285 | 0.261 | 92 |
| 24 | 0.167 | 0.245 | 0.0830 | 0.0282 | 1.0282 | 0.148 | 0.283 | 0.3720 | 131 |
| Group 4: 0.5% Lotemax Gel | | | | | | | | | |
| 0.0833 | 2.95 | 4.04 | 1.51 | 1.28 | 2.28 | 2.22 | 2.38 | 1.01 | 42 |
| 0.25 | 0.943 | 1.73 | 0.758 | 0.801 | 1.801 | 0.661 | 1.120 | 0.512 | 46 |
| 0.5 | 0.417 | 0.699 | 0.518 | 1.00 | 2.00 | 0.554 | 0.865 | 0.592 | 68 |
| 1 | 0.403 | 0.478 | 2.51 | 0.677 | 1.677 | 0.687 | 1.070 | 0.841 | 79 |
| 2 | 0.0665 | 0.220 | 0.201 | 0.158 | 1.158 | 0.441 | 0.374 | 0.403 | 108 |
| 4 | 0.166 | 0.202 | 0.114 | 0.379 | 1.379 | 0.513 | 0.459 | 0.475 | 103 |
| 8 | 0.380 | 0.193 | 0.249 | 0.134 | 1.134 | 0.0643 | 0.359 | 0.395 | 110 |
| 12 | 0.177 | 0.156 | 0.393 | 0.233 | 1.233 | 0.348 | 0.423 | 0.4080 | 96 |
| 24 | 0.0755 | 0.0664 | 0.00796 | 0.0315 | 1.0315 | 0.0788 | 0.2150 | 0.4010 | 187 |

Figure 32

Aqueous Humor

| Time (h) | Rabbit 1 (OD) | Rabbit 1 (OS) | Rabbit 2 (OD) | Rabbit 2 (OS) | Rabbit 3 (OD) | Rabbit 3 (OS) | Mean | SD | CV% |
|---|---|---|---|---|---|---|---|---|---|
| Group 1: 0.38% Submicron Formulation | | | | | | | | | |
| 0.0833 | 0.00388 | 0.00819 | 0.00452 | 0.00242 | 0.00539 | 0.00364 | 0.00467 | 0.00198 | 42 |
| 0.25 | 0.0131 | 0.0138 | 0.0180 | 0.0131 | 0.0150 | 0.0193 | 0.0154 | 0.00266 | 17 |
| 0.5 | 0.0128 | 0.0263 | 0.0209 | 0.0153 | 0.0238 | 0.0339 | 0.0222 | 0.00767 | 35 |
| 1 | 0.0359 | 0.0223 | 0.0292 | 0.0355 | 0.0200 | 0.0258 | 0.0281 | 0.00665 | 24 |
| 2 | 0.00444 | 0.00416 | 0.00415 | 0.00308 | 0.00347 | 0.00504 | 0.00406 | 0.000697 | 17 |
| 4 | 0.000186 | 0.000124 | 0.00103 | 0.000280 | 0.000192 | 0.000440 | 0.000375 | 0.000339 | 90 |
| 8 | 0.0000500[a] | 0.000216 | 0.0000500[a] | 0.000117 | 0.0000500[a] | 0.000327 | 0.000135 | 0.000114 | 84 |
| 12 | 0.0000500[a] | 0.0000500[a] | 0.0000500[a] | 0.000122 | 0.000298 | 0.0000500[a] | 0.000103 | 0.0000996 | 97 |
| 24 | 0.0000500[a] | 0.0000500[a] | 0.0000500[a] | 0.0000500[a] | 0.0000500[a] | 0.0000500[a] | 0.0000500 | 0 | 0 |
| Group 2: 0.38% Micronized Formulation | | | | | | | | | |
| 0.0833 | 0.000856 | 0.00139 | 0.000303 | 0.00203 | 0.00180 | 0.000423 | 0.00113 | 0.000719 | 64 |
| 0.25 | 0.0159 | 0.00612 | 0.00871 | 0.0156 | 0.00675 | 0.0108 | 0.0106 | 0.00428 | 40 |
| 0.5 | 0.0122 | 0.0147 | 0.0150 | 0.0129 | 0.0178 | 0.00853 | 0.0135 | 0.00313 | 23 |
| 1 | 0.00921 | 0.0107 | 0.00674 | 0.00494 | 0.00988 | 0.00666 | 0.00802 | 0.00224 | 28 |
| 2 | 0.00136 | 0.00134 | 0.00199 | 0.00181 | 0.00219 | 0.00234 | 0.00184 | 0.000419 | 23 |
| 4 | 0.000279 | 0.000162 | 0.0000500[a] | 0.000155 | 0.000131 | 0.00100 | 0.000296 | 0.000353 | 119 |
| 8 | 0.0000500[a] | 0.0000500[a] | 0.0000500[a] | 0.0000500[a] | 0.0000500[a] | 0.000140 | 0.0000650 | 0.000367 | 56 |
| 12 | 0.0000500[a] | 0.0000500[a] | 0.0000500[a] | 0.0000500[a] | 0.0000500[a] | 0.0000500[a] | 0.0000500 | 0 | 0 |
| 24 | 0.0000500[a] | 0.0000500[a] | 0.0000500[a] | 0.0000500[a] | 0.0000500[a] | 0.000302 | 0.0000920 | 0.000103 | 112 |

Figure 33

Aqueous Humor

| Time (h) | Rabbit 1 (OD) | Rabbit 1 (OS) | Rabbit 2 (OD) | Rabbit 2 (OS) | Rabbit 3 (OD) | Rabbit 3 (OS) | Mean | SD | CV% |
|---|---|---|---|---|---|---|---|---|---|
| Group 3: 0.75% Unmodified Formulation | | | | | | | | | |
| 0.0833 | 0.00194 | 0.00370 | 0.000960 | 0.00114 | 0.00184 | 0.000870 | 0.00174 | 0.00106 | 61 |
| 0.25 | 0.00739 | 0.0102 | 0.00554 | 0.00798 | 0.00814 | 0.0747 | 0.0190 | 0.0273 | 144 |
| 0.5 | 0.0142 | 0.0155 | 0.0166 | 0.00889 | 0.0170 | 0.0131 | 0.0142 | 0.00299 | 21 |
| 1 | 0.0276 | 0.00801 | 0.00497 | 0.0223 | 0.00861 | 0.0150 | 0.0144 | 0.00895 | 62 |
| 2 | 0.00521 | 0.00219 | 0.00117 | 0.00216 | 0.00259 | 0.00129 | 0.00244 | 0.00147 | 60 |
| 4 | 0.000232 | 0.000426 | 0.000233 | 0.000223 | 0.00173 | 0.000366 | 0.000535 | 0.000591 | 110 |
| 8 | 0.000150 | 0.000540 | 0.000293 | 0.000460 | 0.000105 | 0.000358 | 0.000318 | 0.000170 | 53 |
| 12 | $0.0000500^b$ | $0.0000500^b$ | 0.000151 | 0.000190 | 0.000107 | $0.0000500^b$ | 0.0000997 | 0.0000604 | 61 |
| 24 | $0.0000500^b$ | $0.0000500^b$ | 0.000209 | $0.0000500^b$ | $0.0000500^b$ | 0.000131 | 0.0000900 | 0.0000667 | 74 |
| Group 4: 0.5% Lotemax Gel | | | | | | | | | |
| 0.0833 | 0.00142 | 0.000286 | $0.0134^a$ | 0.000912 | $0.0225^a$ | 0.000383 | 0.000750 | 0.000524 | 70 |
| 0.25 | 0.00799 | 0.00674 | 0.00361 | 0.00295 | 0.00682 | 0.00570 | 0.00564 | 0.00197 | 35 |
| 0.5 | 0.00928 | 0.00938 | 0.00616 | 0.0218 | 0.0137 | 0.00662 | 0.0112 | 0.00586 | 52 |
| 1 | 0.00596 | 0.00655 | 0.00704 | 0.00794 | 0.0146 | 0.00479 | 0.00781 | 0.00349 | 45 |
| 2 | 0.00263 | 0.00120 | 0.0143 | 0.00236 | 0.00125 | 0.00213 | 0.00398 | 0.00509 | 128 |
| 4 | 0.000682 | 0.000535 | 0.00154 | $0.016^a$ | 0.000558 | 0.000826 | 0.000828 | 0.000414 | 50 |
| 8 | 0.000188 | 0.000283 | 0.000316 | $0.0000500^b$ | 0.000198 | $0.0000500^b$ | 0.000181 | 0.000113 | 62 |
| 12 | 0.000334 | 0.000310 | 0.000199 | $0.0000500^b$ | 0.000339 | 0.000163 | 0.000233 | 0.000116 | 50 |
| 24 | $0.0000500^b$ | $0.0000500^b$ | 0.000166 | $0.0000500^b$ | $0.0000500^b$ | $0.0000500^b$ | 0.0000693 | 0.0000474 | 68 |

Figure 34

Iris/Ciliary Body

| Time (h) | Rabbit 1 (OD) | Rabbit 1 (OS) | Rabbit 2 (OD) | Rabbit 2 (OS) | Rabbit 3 (OD) | Rabbit 3 (OS) | Mean | SD | CV% |
|---|---|---|---|---|---|---|---|---|---|
| Group 1: 0.38% Submicron Formulation | | | | | | | | | |
| 0.0833 | 0.0737 | 0.110 | 0.0839 | 0.0264 | 0.0405 | 0.0392 | 0.0623 | 0.0322 | 52 |
| 0.25 | 0.0856 | 0.153 | 0.304 | 0.0921 | 0.184 | 0.171 | 0.165 | 0.0793 | 48 |
| 0.5 | 0.135 | 0.180 | 0.0946 | 0.161 | 0.160 | 0.209 | 0.157 | 0.0391 | 25 |
| 1 | 0.231 | 0.101 | 0.157 | 0.146 | 0.115 | 0.109 | 0.143 | 0.0483 | 34 |
| 2 | 0.0345 | 0.0324 | 0.0238 | 0.0258 | 0.0255 | 0.0329 | 0.0292 | 0.00461 | 16 |
| 4 | 0.00851 | 0.0153 | 0.0131 | 0.00499 | 0.0425 | 0.0130 | 0.0162 | 0.0134 | 83 |
| 8 | 0.00411 | 0.00412 | 0.00474 | 0.0196 | 0.00446 | 0.00971 | 0.00779 | 0.00617 | 79 |
| 12 | 0.00437 | 0.0138 | 0.00101 | 0.00287 | 0.0100 | 0.00140 | 0.00558 | 0.00518 | 93 |
| 24 | 0.00229 | 0.000480[b] | 0.00505 | 0.00167 | 0.00105 | 0.000480[b] | 0.00184 | 0.00172 | 93 |
| Group 2: 0.38% Micronized Formulation | | | | | | | | | |
| 0.0833 | 0.0207 | 0.0843 | 0.0589 | 0.0199 | 0.0233 | 0.0617 | 0.0448 | 0.0272 | 61 |
| 0.25 | 0.104 | 0.266 | 0.0821 | 0.100 | 0.0527 | 0.152 | 0.126 | 0.0758 | 60 |
| 0.5 | 0.0821 | 0.0728 | 0.0866 | 0.0666 | 0.165 | 0.0610 | 0.0890 | 0.0384 | 43 |
| 1 | 0.0489 | 0.0468 | 0.0529 | 0.0706 | 0.0464 | 0.0395 | 0.0509 | 0.0106 | 21 |
| 2 | 0.0152 | 0.0230 | 0.0395 | 0.0261 | 0.0174 | 0.0219 | 0.0239 | 0.00861 | 36 |
| 4 | 0.0184 | 0.0123 | 0.00902 | 0.134[a] | 0.00698 | 0.0122 | 0.0118 | 0.00433 | 37 |
| 8 | 0.00392 | 0.0376 | 0.00260 | 0.0278 | 0.00378 | 0.00305 | 0.0131 | 0.0155 | 118 |
| 12 | 0.00248 | 0.00343 | 0.00164 | 0.00148 | 0.00942 | 0.00981 | 0.00471 | 0.00386 | 82 |
| 24 | 0.00769 | 0.00104 | 0.00663 | 0.00101 | 0.00254 | 0.0148 | 0.00562 | 0.00532 | 95 |

Figure 35

Iris/Ciliary Body

| Time (h) | Rabbit 1 (OD) | Rabbit 1 (OS) | Rabbit 2 (OD) | Rabbit 2 (OS) | Rabbit 3 (OD) | Rabbit 3 (OS) | Mean | SD | CV% |
|---|---|---|---|---|---|---|---|---|---|
| Group 3: 0.75% Unmodified Formulation | | | | | | | | | |
| 0.0833 | 0.110 | 0.0343 | 0.148 | 0.0375 | 0.187 | 0.252 | 0.128 | 0.0855 | 67 |
| 0.25 | 0.0566 | 0.0886 | 0.233 | 0.0587 | 0.224 | 0.869 | 0.255 | 0.311 | 122 |
| 0.5 | 0.0634 | 0.699 | 0.123 | 0.283 | 0.0770 | 0.165 | 0.235 | 0.241 | 103 |
| 1 | 0.163 | 0.0879 | 0.0627 | 0.142 | 0.119 | 0.144 | 0.120 | 0.0380 | 32 |
| 2 | 0.0280 | 0.0195 | 0.0138 | 0.0249 | 0.0258 | 0.0238 | 0.0226 | 0.00516 | 23 |
| 4 | 0.00663 | 0.0475 | 0.0382 | 0.00620 | 0.0520 | 0.0137 | 0.0274 | 0.0209 | 76 |
| 8 | 0.0322 | 0.00636 | 0.0108 | 0.0397 | 0.00751 | 0.0232 | 0.0200 | 0.0140 | 70 |
| 12 | 0.00357 | 0.00293 | 0.00555 | 0.00545 | 0.00294 | 0.00238 | 0.00380 | 0.00137 | 36 |
| 24 | 0.00322 | 0.00388 | 0.00437 | 0.00166 | 0.00212 | 0.00226 | 0.00292 | 0.00107 | 37 |
| Group 4: 0.5% Lotemax Gel | | | | | | | | | |
| 0.0833 | 0.0340 | 0.0156 | 0.0899 | 0.0377 | 0.332 | 0.104 | 0.102 | 0.118 | 116 |
| 0.25 | 0.0932 | 0.0729 | 0.0622 | 0.0653 | 0.0839 | 0.137 | 0.0858 | 0.0277 | 32 |
| 0.5 | 0.0658 | 0.0580 | 0.0515 | 0.0910 | 0.128 | 0.0828 | 0.0795 | 0.0280 | 35 |
| 1 | 0.0466 | 0.0786 | 0.0397 | 0.0348 | 0.0912 | 0.0766 | 0.0613 | 0.0237 | 39 |
| 2 | 0.0172 | 0.0257 | 0.0156 | 0.0212 | 0.0113 | 0.0563 | 0.0246 | 0.0163 | 66 |
| 4 | 0.00576 | 0.0189 | 0.170 | 0.00883 | 0.0193 | 0.102 | 0.0541 | 0.0672 | 124 |
| 8 | 0.00429 | 0.00821 | 0.00650 | 0.0142 | 0.00495 | 0.00833 | 0.00775 | 0.00356 | 46 |
| 12 | 0.00482 | 0.00755 | 0.00395 | 0.00199 | 0.00663 | 0.00735 | 0.00538 | 0.00219 | 41 |
| 24 | $0.000480^c$ | $0.000480^c$ | $0.000480^c$ | 0.00101 | $0.000480^c$ | 0.00197 | 0.000817 | 0.000603 | 74 |

Aqueous Humor

Aqueous Humor

Aqueous Humor

Iris/Ciliary Body

Figure 40

Cornea

Bulbar Conjunctiva

Figure 42

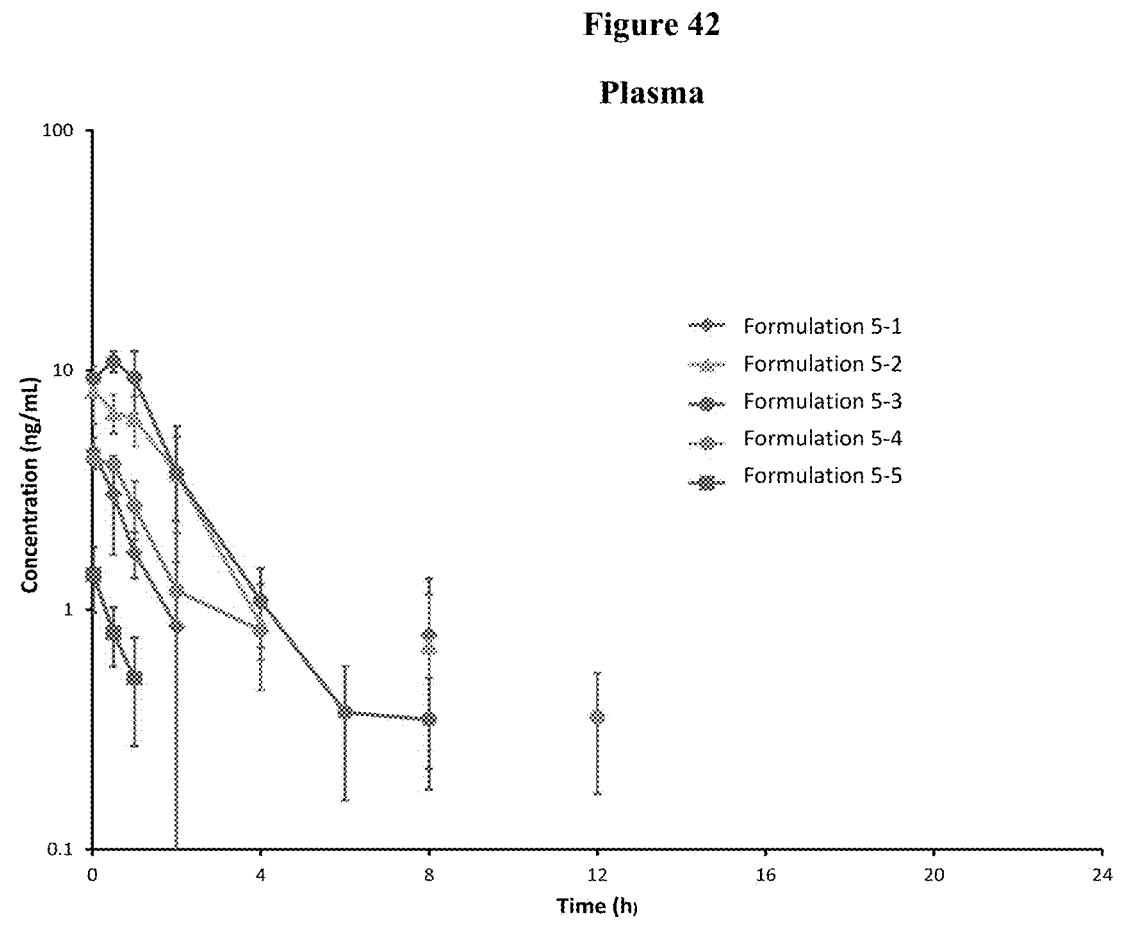

Plasma

OPHTHALMIC SUSPENSION COMPOSITION

BACKGROUND

This invention relates to an ophthalmic suspension composition, especially an ophthalmic suspension composition containing a corticosteroid that provides improved therapeutic efficacy.

Ophthalmic compositions are used to provide relief of a variety of ocular conditions and ocular disease states. Often, ophthalmic compositions are administered or instilled to the eye via eye drops from a multi-dose container in the form of solutions, suspensions, ointments or gels. If the ophthalmic active component is sufficiently soluble in water, the formulation may have the form of a solution eye drop product. However, if the solution product has too low of a viscosity, e.g., less than about 30 cp (or mPa s), upon instillation the ophthalmic active can be rapidly discharged from the pre-corneal area of the eye because of lacrimal secretion and nasolacrimal drainage. As a result, it has been estimated that approximately 80-99% of the ophthalmic active component is simply washed or flushed from the eye before the active actually contacts the desired ocular tissue to achieve its desired clinical effect. The poor residence time of the active in the eye thus requires frequent instillation or use of a more concentrated active product to achieve the desired clinical effect. To lengthen the residence time of ophthalmic active, and thus, to enhance the bioavailability of the ophthalmic active per instillation, non-solution based ophthalmic vehicles have been developed. Examples of such ophthalmic vehicles include ointments, suspensions, and aqueous gels. However, these ophthalmic vehicles can have their drawbacks as well. For example, the use of ointments often causes blurred vision just after instillation. In some instances, the patient can sense a "goopy feeling" in their eyes, which is undesirable.

Some ophthalmic formulations have the form of the so-called in situ gel-forming systems. These ophthalmic vehicles can extend precorneal residence time and improve ocular bioavailability of the ophthalmic active. Typically, in situ gel-forming systems are aqueous solutions containing a polymer system. The ophthalmic products tend to exist as a low-viscosity liquid during storage in the dispenser container and form a gel upon contact with tear fluid. The liquid-to-gel transition can be triggered by a change in temperature, pH, ionic strength, or the presence of tear proteins, depending on the particular polymer system employed. Although a stiff gel can have an extended residence in the eye and assist in promoting a higher drug bioavailability, and perhaps enhance clinical outcome per instillation, such in situ gel forming systems, like the ointments, can interfere adversely with vision and result in patient dissatisfaction. In addition, such compositions must often be formulated at significantly acidic pH, which is not comfortable upon installation in the eye of the patient.

In some formulations, the ophthalmic active is virtually, or completely, insoluble in an aqueous solution-based formulation. For example, U.S. Pat. Nos. 5,538,721 and 4,540,930 describe a pharmaceutical composition comprising an amino-substituted steroid therapeutic agent, and an effective stabilizing amount of lightly cross-linked carboxy-containing polymer. Cyclodextrin has also been used to at least partially solubilize the therapeutic agent in an aqueous medium.

Lotemax® (loteprednol etabonate (LE) ophthalmic gel, 0.5% LE) (Bausch & Lomb Incorporated) contains 5 mg/g of loteprednol etabonate, as a sterile preserved ophthalmic gel suspension, and has proven effective for the treatment of post-operative inflammation and pain following ocular surgery. Lotemax® ophthalmic gel, 0.5% LE, contains boric acid, edetate disodium dihydrate, glycerin, polycarbophil, propylene glycol, sodium chloride, tyloxapol, water, and sodium hydroxide to adjust pH between 6 and 7, and is preserved with benzalkonium chloride (BAK) 0.003%.

DUREZOL® (difluprednate ophthalmic emulsion 0.05%) (Alcon Laboratories, Inc.), a sterile preserved ophthalmic emulsion for topical ophthalmic administration, has proven effective for the treatment of inflammation and pain associated with ocular surgery, and is also indicated for the treatment of endogenous anterior uveitis. DUREZOL® ophthalmic emulsion contains difluprednate (0.05%), boric acid, castor oil, glycerin, sodium acetate, sodium EDTA, sodium hydroxide to adjust pH, polysorbate 80 and water, and is preserved with sorbic acid 0.1%

SUMMARY OF THE INVENTION

This invention provides an ophthalmic suspension comprising an ophthalmic active ingredient suspended in a formulation vehicle, wherein the ophthalmic active ingredient is present as particles that have $D_{v90} < 5$ μm and $D_{v50} < 1$ μm. $D_{v90}$ is the particle diameter below which particles having 90% of the cumulative volume of all the particles are present, and $D_{v50}$ is the particle diameter below which particles having 50% of the cumulative volume of all the particles are present.

In one aspect, the active ingredient comprises an ophthalmic active pharmaceutical ingredient ("API"). In another aspect, the ophthalmic API comprises an anti-inflammatory agent. In still another aspect, the ophthalmic API comprises a steroid (also known in the art as glucocorticosteroid or corticosteroid). In yet another aspect, the ophthalmic API comprises a nonsteroidal anti-inflammatory drug ("NSAID").

The formulation vehicle comprises a suspending agent and a non-ionic cellulose derivative. The suspending agent may comprise a carboxyvinyl polymer, such as polycarbophil or carbomer. The non-ionic cellulose derivative may be hydroxypropylmethyl cellulose.

The suspension may be storage stable for at least one year, or for at least two years.

The ophthalmic active ingredient may be a corticosteroid, such as loteprednol etabonate or difluprednate. The active ingredient may be a non-steroid, such as nepafenac.

The formulation vehicle may further comprise a preservative and/or a surfactant.

According to various aspects, the formulation vehicle comprises polycarbophil, hydroxypropylmethyl cellulose, benzalkonium chloride, a poloxamer surfactant, glycerin, propylene glycol, and a borate buffer agent.

The suspension may have the form of a gel at room temperature that forms a liquid upon instillation in an eye.

According to various aspects, the ophthalmic active ingredient may be present as particles having $D_{v90} < 3$ μm and $D_{v50} < 1$ μm, or present as particles having $D_{v90} < 3$ μm and $D_{v50} < 0.6$ μm, or present as particles having $D_{v90} < 1$ μm.

In another aspect, this invention provides a method of treating an ophthalmic inflammatory condition that comprises administering to an eye of a patient in need of said treating a suspension according to any of the aforementioned aspects. The suspension may be administered at a frequency of one or two times per day, or at a frequency of three or four times per day. The ophthalmic inflammatory condition may be inflammation resulting from post-ocular surgery or from allergic reaction.

BRIEF DESCRIPTION OF THE FIGURES

FIG. 3 shows particle size distribution of Bead Milled vs. 30 minute-Microfluidizer samples.

FIG. 4 shows particle size distribution of Bead Milled vs. 30-180 minute-Microfluidizer samples.

FIG. 26 lists Individual and Summary Statistics for LE Concentrations (μg/g) in Tear Fluid after a Single Topical Ocular Administration to Rabbits (Groups 1 and 2).

FIG. 27 lists Individual and Summary Statistics for LE Concentrations (μg/g) in Tear Fluid after a Single Topical Ocular Administration to Rabbits (Groups 3 and 4).

FIG. 28 lists Individual and Summary Statistics for LE Concentrations (μg/g) in Bulbar Conjunctiva after a Single Topical Ocular Administration to Rabbits (Groups 1 and 2).

FIG. 29 lists Individual and Summary Statistics for LE Concentrations (μg/g) in Bulbar Conjunctiva after a Single Topical Ocular Administration to Rabbits (Groups 3 and 4).

FIG. 30 lists Individual and Summary Statistics for LE Concentrations (μg/g) in Cornea after a Single Topical Ocular Administration to Rabbits (Groups 1 and 2).

FIG. 31 lists Individual and Summary Statistics for LE Concentrations (μg/g) in Cornea after a Single Topical Ocular Administration to Dutch Belted Rabbits (Groups 3 and 4).

FIG. 32 lists Individual and Summary Statistics for LE Concentrations (μg/g) in Aqueous Humor after a Single Topical Ocular Administration to Rabbits (Groups 1 and 2).

FIG. 33 lists Individual and Summary Statistics for LE Concentrations (μg/g) in Aqueous Humor after a Single Topical Ocular Administration to Rabbits (Groups 3 and 4).

FIG. 34 lists Individual and Summary Statistics for LE Concentrations (μg/g) in Iris/Ciliary Body after a Single Topical Ocular Administration to Rabbits (Groups 1 and 2).

FIG. 35 lists Individual and Summary Statistics for LE Concentrations (μg/g) in Iris/Ciliary Body after a Single Topical Ocular Administration to Dutch Belted Rabbits (Groups 3 and 4).

Figure 40:
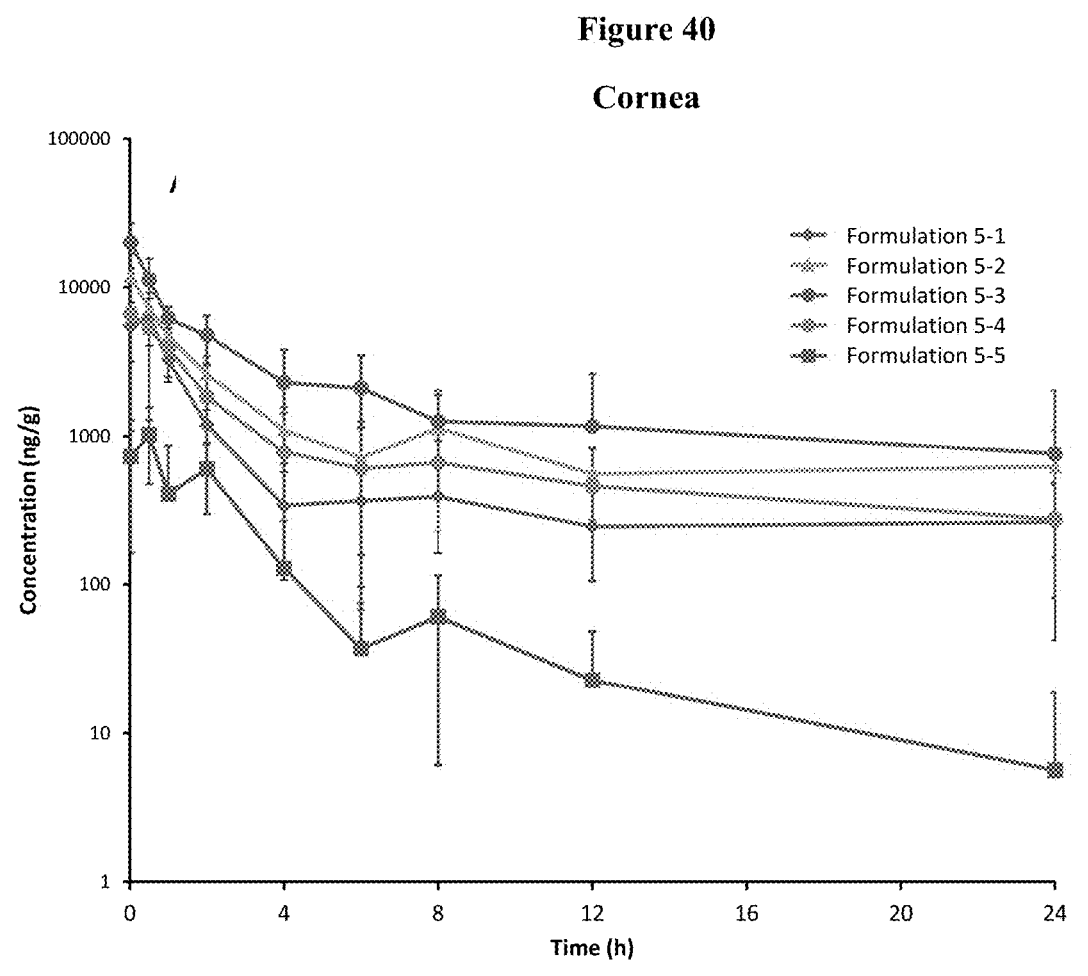

FIG. 40 shows Difluprednate Metabolite Concentrations in Cornea after a Single Topical Ocular Administration of Difluprednate to Dutch Belted Rabbits FIG. 42 shows Difluprednate Metabolite Concentrations in Plasma after a Single Topical Ocular Administration of Difluprednate to Dutch Belted Rabbits

DETAILED DESCRIPTION

Figure 1:
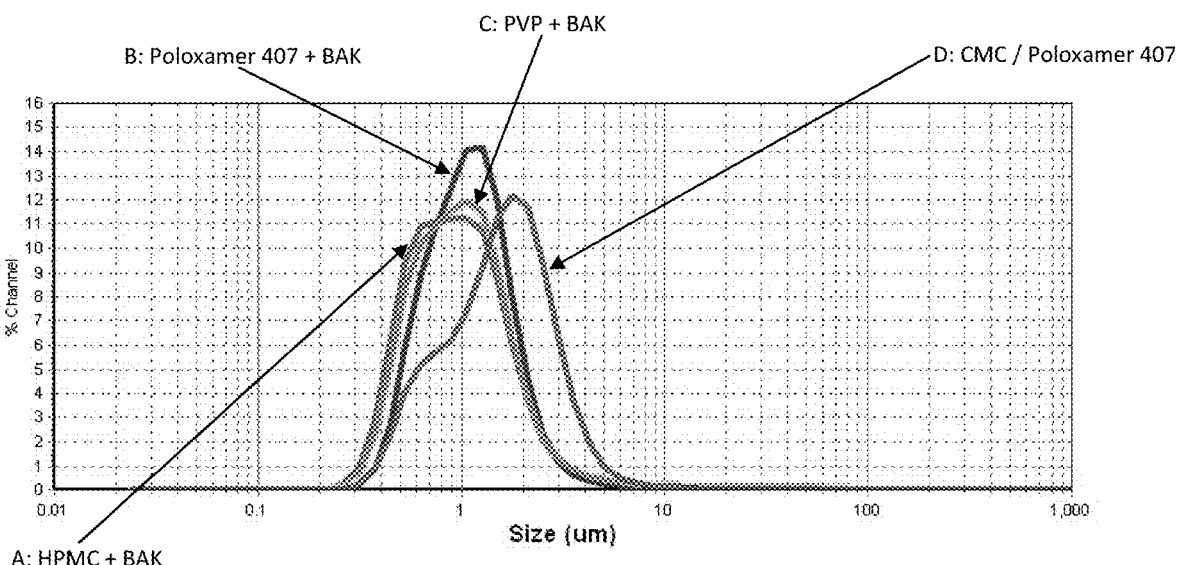
FIG. 1 shows particle size distribution of LE samples milled in a microfluidizer.

A variety of ophthalmic active ingredients may be employed in this invention. Generally, ophthalmic active ingredients include any active ingredient for the treatment of dry eye, allergy, glaucoma, inflammation, or infection.

A first class of ophthalmic active pharmaceutical ingredients (APIs) is steroids, also known in the art as glucocorticosteroids or corticosteroids, especially for the treatment of ocular inflammatory conditions. Examples include loteprednol etabonate, dexamethasone, fluoromethalone, prednisolone and difluprednate. Another class of ophthalmic APIs is NSAIDs, such as nepafenac. Other classes of ophthalmic APIs include anti-bacterial agents, such as besifloxacin, and immunosuppressants, such as cyclosporine.

According to various aspects, the corticosteroid suspended in the formulation vehicle is selected from: dexamethasone at concentrations of 0.1% to 0.2% by weight, fluoromethalone at concentrations of 0.05% to 0.25% by weight, prednisolone at concentrations of 0.1% to 1% by weight, loteprednol etabonate at concentrations of 0.1% to 0.5% by weight and difluprednate at concentrations of 0.01 to 0.1% by weight. Alternately, according to various aspects, the non-steroid suspending in the formulation vehicle is nepafenac at concentrations of 0.1 to 0.5% by weight.

Generally, the suspensions of the invention will include an ophthalmic active ingredient that has a solubility in water at 25° C. and pH of 7 that is less than 10% of the formulated concentration in mg/mL in the ophthalmic formulation. For example, if the ophthalmic active ingredient is present in an ophthalmic formulation at a concentration of 0.1 mg/mL, the ophthalmic active will have a solubility in water at 25° C. and a pH of 7 of less than 0.1×(0.1 mg/mL), i.e., less than 0.01 mg/mL. Likewise, for an ophthalmic active that is present in an ophthalmic formulation at a concentration of 10 mg/mL, the ophthalmic active ingredient will have a solubility in water at 25° C. and a pH of 7 of less than 0.1×(10 mg/mL), i.e., less than 1.0 mg/mL. Accordingly, the water solubility of a specific agent in the suspension and the agent's concentration in the suspension in mg/mL are related with respect to formation of a suspension. In other words, an ophthalmic active ingredient present at a relatively high concentration in a suspension can have a somewhat greater water solubility than another agent with a lower water solubility present in another suspension at a lower concentration, but because of the higher concentration in the former suspension a significant portion of the former agent remains suspended in the formulation.

According to various aspects, the ophthalmic active ingredient is loteprednol etabonate. Loteprednol etabonate (also referred to herein as "LE") is a known compound and can be synthesized by methods disclosed in U.S. Pat. No. 4,996,335, the entire contents of which are hereby incorporated by reference in the present specification. According to various aspects, the concentration of LE in the formulation vehicle is in the range from 0.1 wt. % to 2 wt. %, or from 0.14 wt. % to 1.5 wt. %, or from 0.2 wt. % to 1 wt. %, or from 0.2 wt. % to 0.5 wt. %. A specific concentration of LE may be 0.38 wt %.

Another ophthalmic active ingredient is difluprednate. Difluprednate (also referred to herein as "DFBA") is a derivative of prednisolone and a known compound, and can be synthesized by methods known in the art. According to various aspects, the concentration of DFBA in the formulation vehicle is in the range from 0.01 to 0.1% by weight, or from 0.02 to 0.07 wt. A specific concentration of DFBA may be 0.05 wt %.

The formulation vehicle includes at least one suspending agent. One class of suspending agents are polymers prepared from at least about 90%, or from at least about 95%, by weight, based on the total weight of monomers present, of one or more carboxyl-containing monoethylenically unsaturated monomers. Acrylic acid is a suitable carboxyl-containing monoethylenically unsaturated monomer, but other ethylenically unsaturated, polymerizable carboxyl-containing monomers may be employed. These include: methacrylic acid, ethacrylic acid, β-methylacrylic acid (crotonic acid), cis-α-methylcrotonic acid (angelic acid), trans-α-methylcrotonic acid (tiglic acid), α-butylcrotonic acid, α-phenylacrylic acid, α-benzylacrylic acid, α-cyclohexylacrylic acid, β-phenylacrylic acid (cinnamic acid), coumaric acid (o-hydroxycinnamic acid), umbellic acid (p-hydroxycoumaric acid), and the like, which can be used in addition to, or instead of, acrylic acid.

The carboxyl-containing polymers prepared from these monoethylenically unsaturated monomers may be lightly cross-linked by employing a small percentage, i.e., from about 0.5% to about 5%, or from about 0.2% to about 3%, based on the total weight of monomers present, of a polyfunctional cross-linking agent. Such cross-linking agents including non-polyalkenyl polyether difunctional cross-linking monomers, such as: divinyl glycol; 3,4-dihydroxy-hexa-1,5-diene; 2,5-dimethyl-1,5-hexadiene; divinylbenzene; N,N-diallylacrylamide; N,N-dialkylmethacrylamide; and the like.

Various lightly cross-linked polymers are commercially available, or may be generally prepared by suspension or emulsion polymerization, using conventional free radical polymerization catalysts. In general, such polymers will range in molecular weight from about 250,000 to about 4,000,000, or from about 500,000 to about 2,000,000.

The lightly cross-linked polymers can be made from a carboxyl-containing monomer or monomers as the sole monoethylenically unsaturated monomer present, together with the cross-linking agent or agents. They can also be polymers in which up to about 40%, or within the range of about 0% to about 20% by weight, of the carboxyl-containing monoethylenically unsaturated monomer or monomers has been replaced by one or more non-carboxyl-containing monoethylenically unsaturated monomers containing only physiologically and ophthalmologically innocuous substituents, including acrylic and methacrylic acid esters such as methyl methacrylate, ethyl acrylate, butyl acrylate, 2-ethylhexylacrylate, vinyl acetate, 2-hydroxyethylmethacrylate, 3-hydroxypropylacrylate, and the like.

Various lightly cross-linked carboxy-containing polymers are known in the art. For example, those disclosed in Robinson U.S. Pat. No. 4,615,697, International Publication No. WO 89/06964, and Davis et al U.S. Pat. No. 5,192,535. An example of lightly cross-linked polymers are acrylic acid polymers wherein the cross-linking monomer is 3,4-dihydroxyhexa-1,5-diene or 2,5-dimethylhexa-1,5-diene.

Another class of lightly cross-linked polymers are carboxyl-containing polymer prepared by suspension polymerization of acrylic acid and divinyl glycol, including NOVEON AA-1 polycarbophil (available from Lubrizol). Other lightly cross-linked carboxy-containing polymers include various carbomers, such as Carbopol carbomers (available from Lubrizol). According to various aspects, the suspending agent is a carboxyvinyl polymer selected from polycarbophil and carbomer.

The suspending agent serves to ensure the ophthalmic active ingredient remains in suspension in the formulation vehicle. The formulation vehicle provides a storage-stable, suspension of the ophthalmic active ingredient, such as in the form of a gel. However, once instilled into the eye as eye drops, the gel gradually transitions to a liquid form, i.e., it loses its gel character due to the shear thinning properties of the gel. Following instillation, the eyelid applies shear to the formulation when the eye blinks, and this shear reduces drastically the viscosity, thereby avoiding the sticky, "goopy" sensation as found in many ointments and eye drops intended to remain in gel form while in the eye. However, once eyelid movement ceases, thereby eliminating the shear force, viscosity is no longer reduced, helping to maintain residence of the formulation on the eye. Eventually, the gel transitions entirely to liquid. In certain aspects, the ophthalmic suspension has a yield point, at which point below the composition is a solid gel, of 2-8 Pascals, and more suitably 3-5 Pa.

The term "storage-stable" denotes that the API will remain effectively suspended in the formulation vehicle for an extended period of time without having to stir or shake the packaged composition. In other words, agitation of the formulation in its package is not required to re-suspend the API in the formulation vehicle. In contrast, non-storage-stable suspensions require a user to shake the packaged composition before instillation so that the API is uniformly distributed in the carrier vehicle; however, if the user neglects to shake the package, the user may not instill a consistent and proper dosage.

Accordingly, the storage-stable ophthalmic suspensions of this invention will consistently deliver 90% to 110% of a predetermined dosage of pharmaceutical active per eye drop, without a patient having to agitate the suspension in its container.

According to various aspects, the composition is storage-stable in its package for at least a year, in which case the shelf-life of the product is one year. According to other aspects, the composition is storage-stable in its package for at least two years, in which case the shelf-life of the product is two years.

According to various aspects, the formulation vehicle includes a non-ionic cellulose derivative as a supplemental suspending agent. Representative agents include hydroxypropylmethyl cellulose ("HPMC") or hydroxypropylcellulose ("HPC").

The vehicle formulations described herein can also include various other ingredients, including but not limited to surfactants, tonicity agents, buffers, preservatives, chelating agents, co-solvents and viscosity-building agents.

Surfactants that can be used are surface-active agents that are acceptable for ophthalmic applications. Useful surface active agents include polysorbate 80 (such as Tween® 80 surfactant from ICI America Inc), tyloxapol, and various poloxamer surfactants including poloxamer 188 (such as Pluronic® F-68 surfactant available from BASF) and poloxamer 407 (such as Pluronic® F127 available from BASF). These surfactants are nonionic alkaline oxide condensates of an organic compound which contains hydroxyl groups. The concentration in which the surface active agent may be used is only limited by neutralization of the bactericidal effects on the accompanying preservatives (if present), or by concentrations which may cause eye irritation.

Various tonicity agents may be employed to adjust the tonicity of the formulation. Examples are sodium chloride, potassium chloride, magnesium chloride, calcium chloride and nonionic diols, such as glycerol and propylene glycol, dextrose and/or mannitol. These agents may be added to the formulation to approximate physiological tonicity. Such an amount of tonicity agent will vary, depending on the particular agent to be added. In general, however, the formulations will have a tonicity agent in an amount sufficient to cause the final formulation to have an ophthalmically acceptable osmolality (generally about 150-450 mOsm/kg). According to various aspects, a nonionic tonicity agent that also functions as a demulcent may be employed.

An appropriate buffer system may be added to the formulations to prevent pH drift under storage conditions. Such buffers include phosphate buffers (e.g., sodium dihydrogen phosphate), acetate buffers (e.g., sodium acetate), citrate buffers (e.g., sodium citrate and/or citric acid) and borate buffers (e.g., sodium borate and/or boric acid) The particular concentration of the buffer will vary, depending on the specific agent employed.

Topical ophthalmic products are typically packaged in multidose form, in which case a preservative is generally required to prevent microbial contamination during use. Suitable preservatives include: biguanides, hydrogen peroxide, hydrogen peroxide producers, benzalkonium chloride, chlorobutanol, benzododecinium bromide, phenylethyl alcohol, sorbic acid, polyquaternium-1, and other agents known in the art. Such preservatives are typically employed at a level of from 0.001 to 1% (w/w). A chelating agent, such as edetate disodium, may be included to enhance the efficacy of the antimicrobial agent used as the preservative. In the case where the ophthalmic suspension is packaged in a unitary dose form, the sterile suspension generally does not require a preservative.

Supplemental co-solvents or viscosity-building agents may be added to the formulation vehicles. Such materials may be included to provide lubrication, to make the formulation vehicle approximate the consistency of endogenous tears, to aid in natural tear build-up, or otherwise to provide temporary relief of dry eye symptoms and conditions upon ocular administration. Supplemental viscosity-building agents include polymeric polyols, such as, polyethylene glycol, dextrans such as dextran 70, water soluble proteins such as gelatin, polyvinyl alcohols, polyvinylpyrrolidones, and polysaccharides such as hyaluronic acid and its salts and chondroitin sulfate and its salts.

A representative gel suspension of this invention comprises or consists essentially of, or consists of the following composition:

| Component/Function | % By Weight of Total Composition |
|---|---|
| API Submicron Particles | 0.05-2% |
| Suspending Agent | 0.01-5% |
| Non-ionic cellulose derivative | 0.01-1% |
| Preservative | 0-1% |
| Chelating Agent | 0-1% |
| Tonicity Agent | 0-1% |
| Surfactant | 0.01-5% |
| Demulcent/Tonicity Agent | 0.01-5% |
| Buffer Agent | 0.001-2% |
| Water as Diluent | qs to 100% |
| pH Adjuster | qs to pH of 6-8 |

According to various aspects, a gel suspension comprises or consists essentially of, or consists of the following composition:

| Component/Function | % By Weight of Total Composition |
|---|---|
| Corticosteroid API Submicron Particles | 0.04-2% |
| Carboxyvinyl Polymer Suspending Agent | 0.01-2% |
| Non-ionic Cellulose Derivative | 0.01-2% |
| Preservative | 0.001-1% |
| Chelating Agent | 0.01-1% |
| Tonicity Agent | 0.01-1% |
| Nonionic Surfactant | 0.01-5% |
| Nonionic Diol Demulcent/Tonicity Agent | 0.01-2% |
| Buffer Agent | 0.001-2% |
| Water for injection | qs to 100% |
| Sodium hydroxide | qs to pH about 6.3-7.0 |

According to various other aspects, a gel suspension comprises or consists essentially of, or consists of the following composition:

| Component | % By Weight of Total Composition |
|---|---|
| Loteprednol Etabonate Submicron Particles | 0.1-0.4% |
| Polycarbophil | 0.1-0.5% |
| Hydroxypropylmethyl Cellulose | 0.1-0.5% |
| Benzalkonium Chloride (BAK) | 0.001-0.01% |
| Edetate Disodium Dihydrate | 0.01-0.1% |
| Sodium Chloride | 0.01-0.1% |
| Poloxamer Nonionic Surfactant | 0.1-1.0% |
| Glycerin and/or Propylene Glycol | 0.1-2% |
| Borate Buffer | 0.01-1% |
| Water for injection | qs to 100% |
| Sodium hydroxide | qs to pH about 6.3-7.0 |

A first composition, according to various aspects, comprises or consists essentially of, or consists of the following Composition A:

| Component | Concentration (mg/mL) Composition A |
|---|---|
| Loteprednol Etabonate Submicron Particles | 3.80 |
| Polycarbophil, USP | 3.75 |
| Hydroxypropylmethyl Cellulose E4M | 2.50 |
| BAK 50%[a], EP/USP/NF | 0.06 |
| Edetate Disodium Dihydrate, USP | 0.55 |
| Sodium Chloride, USP | 0.50 |
| Poloxamer 407 | 2.00 |
| Glycerin, USP | 8.80 |
| Propylene glycol, USP | 4.40 |
| Boric Acid, NF | 5.00 |
| Water for injection | qs to 1 mL |
| Sodium Hydroxide (2N) | qs to pH 6.5 |

[a]As BAK Solution is 50% aqueous, the final concentration in BAK is 0.03 mg/mL.

(a) As BAK Solution is 50°% aqueous, the final concentration in BAK is 0.03 mg mL.

According to other aspects, a gel suspension comprises or consists essentially of, or consists of the following composition:

| Component | % By Weight of Total Composition |
|---|---|
| Difluprednate Submicron Particles | 0.01-0.1% |
| Carboxyvinyl Polymer Suspending Agent | 0.1-0.5% |
| Hydroxypropylmethyl Cellulose | 0.1-0.5% |
| BAK | 0.001-0.01% |
| Edetate Disodium Dihydrate | 0.01-0.1% |
| Sodium Chloride | 0.01-0.1% |
| Poloxamer Nonionic Surfactant | 0.01-1.0% |
| Glycerin and/or Propylene Glycol | 0.1-2% |
| Borate Buffer | 0.01-1% |
| Water for injection | qs to 100% |
| Sodium hydroxide | qs to pH about 5.3 to 6.7 |

Another composition, according to various aspects, comprises or consists essentially of, or consists of the following Composition B:

| Component | Concentration (mg/mL) Composition B |
|---|---|
| Difluprednate Submicron Particles | 0.5 |
| Polycarbophil, USP | 3.75 |
| Hydroxypropylmethyl Cellulose E4M | 2.50 |
| BAK 50%[a], EP/USP/NF | 0.06 |
| Edetate Disodium Dihydrate, USP | 0.55 |
| Sodium Chloride, USP | 0.50 |
| Poloxamer 407 | 0.26 |
| Glycerin, USP | 8.80 |
| Propylene glycol, USP | 4.40 |
| Boric Acid, NF | 5.00 |
| Water for injection | qs to 1 mL |
| Sodium Hydroxide (2N) | qs to pH 6.0-6.5 |

[a]As BAK Solution is 50% aqueous, the final concentration in BAK is 0.03 mg/mL.

(a) As BAK Solution is 50°% aqueous, the final concentration in BAK is 0.03 mg mL.

Additional compositions, Compositions C and D, comprise, consist essentially of, or consist of:

| Component | Concentration (mg/mL) Composition C | Concentration (mg/mL) Composition D |
|---|---|---|
| Difluprednate Submicron Particles | 0.5 | 0.5 |
| Carbomer | 3 | 3 |
| Hydroxypropylmethyl Cellulose E4M | 2.5 | 2.5 |
| BAK | 0.03 | — |
| Sorbic Acid | | 1 |
| Edetate Disodium Dihydrate, USP | 0.3 | 0.2 |
| Sodium Chloride, USP | 0.5 | 0.3 |
| Poloxamer 407 | 0.26 | 0.26 |
| Glycerin, USP | 8.8 | 1.0 |
| Propylene glycol, USP | 4.4 | 6 |
| Boric Acid, NF | 5 | 1 |
| Water for injection | qs to 1 mL | qs to 1 mL |
| Sodium Hydroxide (2N) | qs to pH about 5.5 | qs to pH about 5.5 |

Additional compositions, Compositions E and F, comprise, consist essentially of, or consist of:

| Component | Concentration (mg/mL) | |
|---|---|---|
| | Composition E | Composition F |
| Nepafenac Submicron Particles | 3.0 | 1.8 |
| Polycarbophil, USP | 3.75 | 3.75 |
| Hydroxypropylmethyl Cellulose E4M | 2.50 | 2.50 |
| BAK 50%[a], EP/USP/NF | 0.06 | 0.06 |
| Edetate Disodium Dehydrate, USP | 0.55 | 0.55 |
| Sodium Chloride, USP | 0.50 | 0.50 |
| Poloxamer 407 | 1.53 | 0.92 |
| Glycerin, USP | 8.80 | 8.80 |
| Propylene glycol, USP | 4.40 | 4.40 |
| Boric Acid, NF | 5.00 | 5.00 |
| Water for injection | qs to 1 mL | qs to 1 mL |
| Sodium Hydroxide (2N) | qs to pH 6.8 | qs to pH 6.8 |

[a]As BAK Solution is 50% aqueous, the final concentration in BAK is 0.03 mg/mL.

(a) As BAK Solution is 50% aqueous, the final concentration in BAK is 0.03 mg/mL.

As mentioned, the ophthalmic suspension of this invention comprises an ophthalmic active ingredient suspended in a formulation vehicle, wherein the ophthalmic active ingredient is present as particles that have $D_{v90} < 5$ μm and $D_{v50} < 1$ μm. $D_{v90}$ is the particle diameter below which particles having 90% of the cumulative volume of all the particles are present, and $D_{v50}$ is the particle diameter below which particles having 50% of the cumulative volume of all the particles are present. $D_{v90}$ and $D_{v50}$ may be measured by light diffraction techniques generally known in the art.

Light diffraction (LD) is a known method for determining the particle size of materials that are suspended in a liquid or dispersed in air. The technique utilizes the principle of light diffraction where particles will diffract (scatter) light at angles which are inversely proportional to their diameters. That is to say, large particles will diffract light at small angles while small particles diffract light at larger angles. In practice, commercially available instruments include a light source, such as a low power laser, illuminates the particles passing through a measurement zone within a sample cell. The cone of diffracted light produced where the beam interacts with the particles produces a stationary diffraction pattern that is focused on detectors, such as two optical detector arrays. The detectors are typically composed of a series of electronically separated photo-elements arranged to measure the radial dispersion of light energy. Amount and direction of the light which strikes these detectors is electronically coded and transmitted to a computer for processing. By taking a measurement over a suitable period of time and using a continuous flux of particles through the illuminated area, a representative light diffraction profile is obtained.

After measuring the diffraction pattern, the commercially available measurement instruments generally include a CUP and software which analyzes the diffraction pattern measurement, background measurement and any required information entered by the operator (e.g., refractive indices, particle shape, spherical or irregular) to calculate a size distribution model which "best fits" the observed diffraction pattern profile. Once this "best fit" is achieved, the instrument will generally provide a print-out or display of the size distribution parameters which characterize the model. Typically, the results are given in terms of a volume size distribution. e.g., $D_{v10}$=x, $D_{v50}$=y, $D_{v90}$=7, etc.

For the ophthalmic suspensions of this invention, an appropriate measurement technique is as follows. 5 grams of the gel is weighed into a flat bottom glass beaker. 208 grams of a 6% saline dispersant is added to the beaker. The contents of the beaker are magnetically stirred, and an the tip of an ultrasonic processor is immersed in below the surface of the contents, and the contents are sonicated while the contents are stirred. Approximately a 3-mL portion of the stirred, sonicated sample is withdrawn, and the entire portion is promptly dispensed into the recirculator bowl of the light diffraction instrument, which contains recirculated dispersant. If necessary, additional portions of the sample suspension may be added until reaching a transmission value of 0.92-0.96. Collection of the sample diffraction pattern is initiated within minutes after final addition of the sample suspension to the recirculator. The desired size distribution (e.g., $D_{v10}$, $D_{v50}$, $D_{v90}$) are generated by the instrument's software. An example of an instrument is the S3500 laser diffractive analyzer available from Microtrac (York, PA, USA and Krefeld, Germany).

Ophthalmic active ingredients with such particle sizes may be obtained by methods generally known in the art. For example, an aqueous slurry, containing the active and the formulation vehicle, may be subjected to fluid micronization or bead milling, for a suitable time to obtain the desired particle size. Representative techniques for fluid micronization and bead milling are provided in Example 1. In Example 1, bead milling was optimized to provide an ophthalmic active ingredient with the desired particle size, but other methods, or variations of the described bead milling methods, may be employed.

The invention will now be further described by way of several examples that are intended to describe but not limit the scope of the invention defined by the claims herein.

Example 1—Milling of API

In the following experiments, two options for particle size reduction of API were investigated: a high pressure homogenizer microfluidizer and bead milling. The high pressure homogenizer microfluidizer employed was Microfluidics model M-110EH microfluidizer. Additionally, various vehicles for milling were investigated. Particle size analyses were determined by light diffraction (LD) unless indicated otherwise.

In a first set of experiments, studies were conducted with the microfluidizer. As summarized in Table 1, various formulations employed 10% loteprednol etabonate (LE) in 1% Polysorbate 20 (Tw20) and 0.5% boric acid with various other excipients, including Tyloxapol (Tylox) surfactant, Pluronic F68 (F68) surfactant, and benzalkonium chloride (BAK). Additionally, a formulation including 1% HPMC (hydroxypropylmethyl cellulose) and 0.2% BAK was tested. The results are shown in Table 1. It was determined from this experiment that Polysorbate 20 was not a critical excipient for milling.

TABLE 1

| Particle Size Distribution of LE Milling in Polysorbate 20 | | | |
|---|---|---|---|
| Sample Vehicle | Dv10 | Dv50 | Dv90 |
| 1% Tw20 + 0.1% HPMC in 0.5% Boric | 0.758 | 1.875 | 3.611 |
| 1% Tw20 + 0.5% F68 in 0.5% Boric Acid | 1.248 | 3.332 | 6.419 |
| 1% Tw20 + 0.5% Tylox in 0.5% Boric Acid | 0.642 | 1.543 | 3.016 |
| 1% Tw20 + 1% HPMC in 0.5% Boric Acid | 0.593 | 1.257 | 2.344 |
| 1% Tw20 + 0.07% BAK in 0.5% Boric Acid | 0.543 | 1.098 | 2.158 |
| 1% HPMC + 0.2% BAK in 0.5% Boric Acid | 0.472 | 0.940 | 2.068 |

In another set of experiments, four milling vehicles were tested, each containing 10% LE as the API. Additionally, the milling vehicles contained the following:

A—0.5% boric acid, 0.2% BAK, 0.5% HPMC E3
B—0.5% boric acid, 0.2% BAK, 0.5% Poloxamer 407
C—0.5% boric acid, 0.2% BAK, 0.5% PVP C30
D—0.5% boric acid, 0.5% CMC LV; 0.2% Poloxamer 407

The samples were milled in the microfluidizer for 20 minutes in a recirculating manner at 25 k psi. Sample B, containing poloxamer 407 with BAK has the narrowest and the most monomodal distribution, as seen in FIG. 1. Sample D, containing CMC/Poloxamer, appeared larger and highly aggregated.

In another set of experiments, API concentration was tested for its effect on milling. Vehicles similar to Sample B above, containing 0.5% Boric acid+0.5% Poloxamer 407+ 0.2% BAK, were employed with either 10%, 20% or 30% LE. The slurries were similarly run in a recirculating manner in the microfluidizer at 25 k psi. Samples were taken for particle size analysis at 10 minute, 20 minutes and 30 minute intervals. The 30-minute sample with 10% LE had suitable

13

Figure 2:
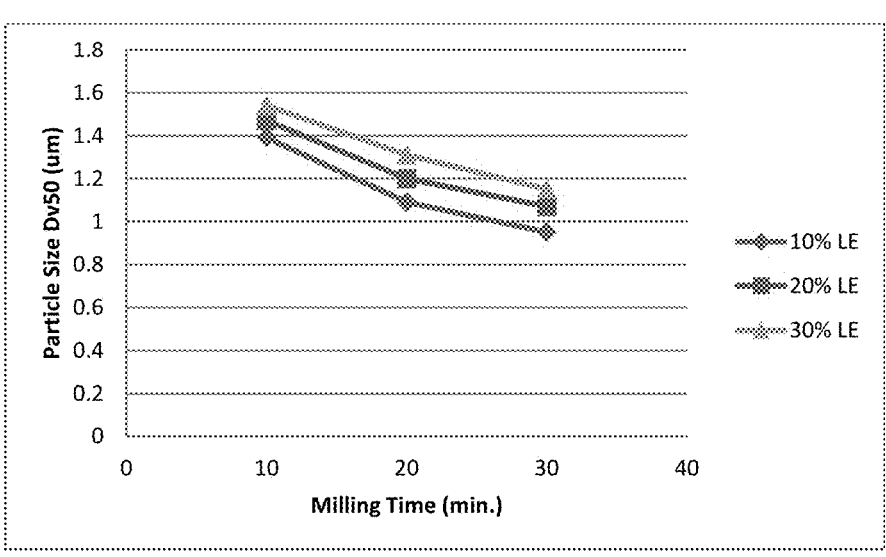
FIG. 2 shows change in particle size $D_{v50}$ over time during milling in a microfluidizer.

14 results. The samples with higher concentrations of API did not appear to be more efficient. The results are reported in FIG. 2.

From previous experience with bead milling, it was known that the use of BAK during bead milling may cause aggregation. Accordingly, this was tested with LE by milling the 30% LE suspension (containing 0.5% Poloxamer 407+ 0.2% BAK) with 0.5-mm zirconium oxide ($ZrO_2$) beads for 20 minutes in a Flacktek mixer. By light microscopy, the particle size distribution looked worse. This may have been due to recrystallization as the vial became quite hot. To better control the temperature during milling, the sample was placed in a wrist shaker and shaken overnight. An additional sample containing 30% LE with Poloxamer 407 but no BAK was also placed on the wrist shaker. The particle size of both bead-milled samples was smaller than the 30-minute microfluidizer samples (containing 0.5% Poloxamer 407+0.2% BAK), with no discernable differences for the bead-milled samples with and without BAK. The data is summarized in FIG. 3.

To further investigate whether milling in the microfluidizer could provide a comparable particle size as bead milling, an additional study was conducted using the 10% LE in the Poloxamer/BAK vehicle, with the slurries milled in the microfluidizer at 25 k psi up to 180 minutes. Samples were taken at 30-minute intervals. At 90 minutes, a particle size of $D_{v90}$ less than 1 µm was achieved. Additional milling time slowly further reduced the particle size but did not yield the smaller particle sizes achievable by bead milling. The results are reported in FIG. 4.

Since the above experiments indicated smaller particle size was obtained by bead milling, additional work was done to further optimize the bead milling process.

Figure 5:
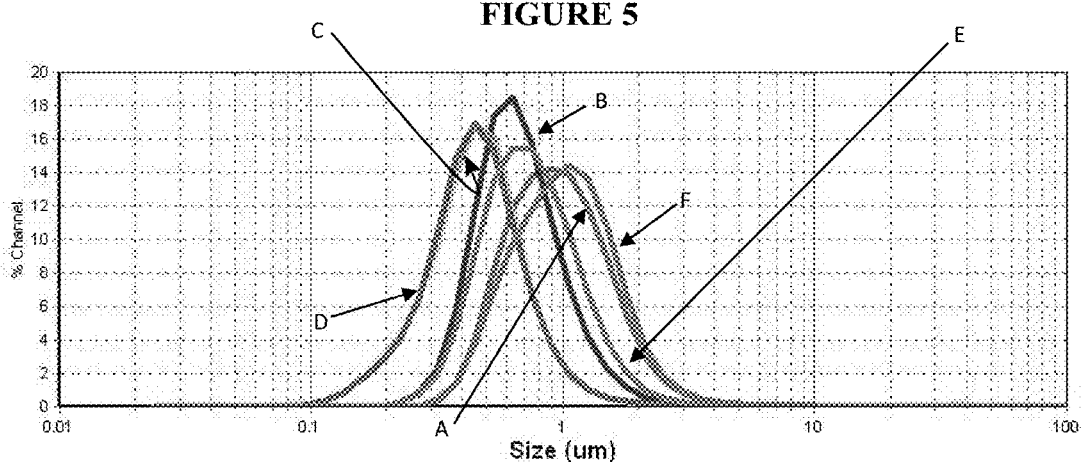
FIG. 5 shows particle size distribution of Bead Milled samples with and without BAK using 2.0-, 1.0- and 0.5-mm bead diameters.

FIG. 5 reports the particle size distribution of the following bead-milled samples, shaken on a wrist shaker for 16 hours with the indicated $ZiO_2$ bead sizes:

A—20% LE, 8% poloxamer F127—2.0-mm beads

B—20% LE, 2% poloxamer F127—1.0-mm beads

C—20% LE, 2% poloxamer F127—0.5-mm beads

D—22% LE, 2.2% poloxamer F127, 0.225% BAK—0.5-mm beads

E—20% LE, 2.2% poloxamer F127, 0.225% BAK—1.0 mm beads

F—20% LE, 2.2% poloxamer F127, 0.225% BAK—2.0-mm beads

The smallest particle size distribution was obtained with the 0.5 mm beads. The use of BAK in the milling slurry had no immediate effect on the particle size.

Figure 6:
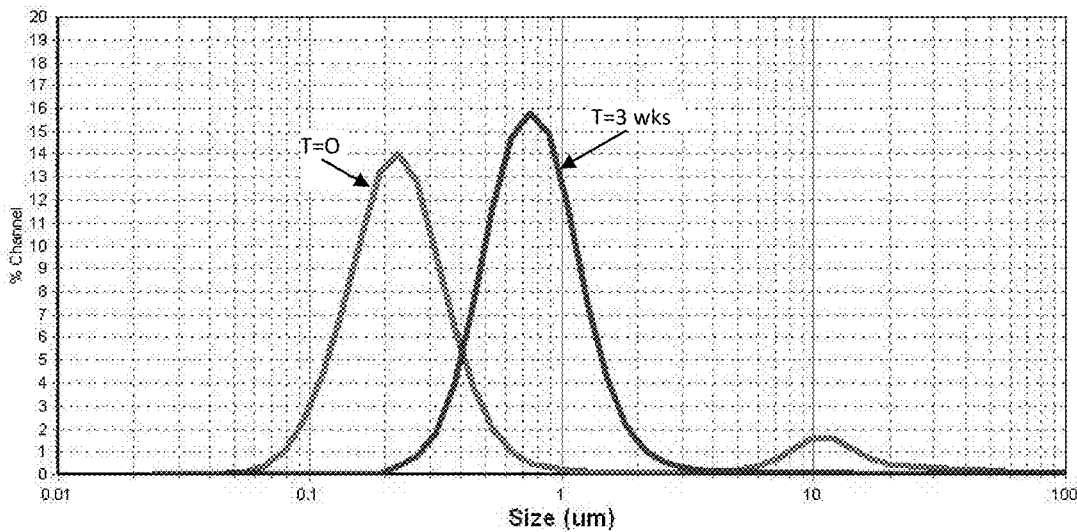
FIG. 6 shows particle size distribution of Bead Milled samples with BAK at T=0 and T=3 weeks.
Figure 7:
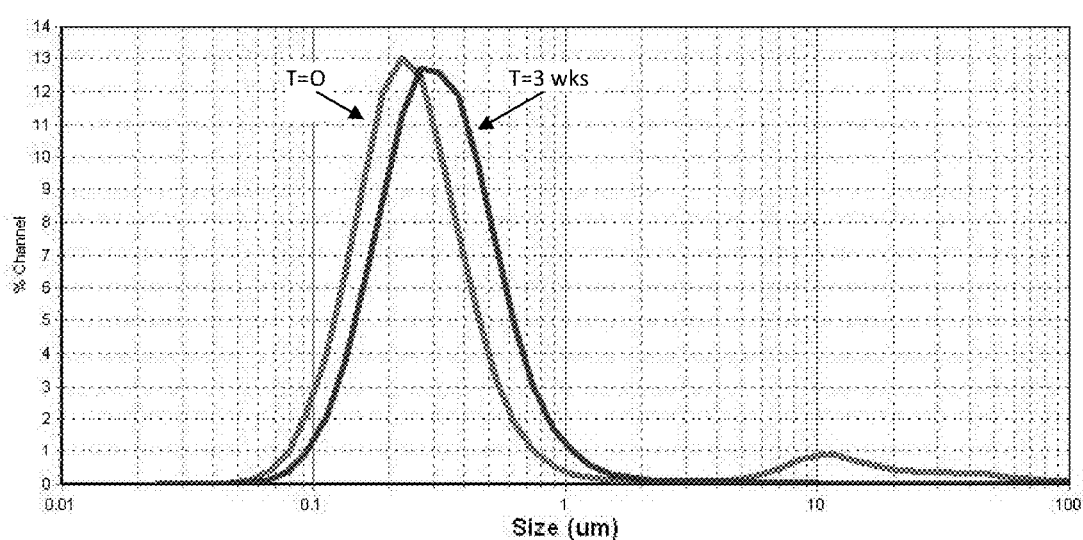
FIG. 7 shows particle size distribution of Bead Milled samples without BAK at T=0 and T=3 weeks.

FIG. 6 reports particle size distribution of bead-milled slurries containing 30% LE, poloxamer 407 and BAK, and FIG. 7 reports particle size distribution of bead-milled slurries containing 30% LE and poloxamer 407 but no BAK, at Time-0 and after three weeks (T=3 wks). The BAK sample (FIG. 6) showed particle growth, whereas there was no significant change in the slurry without BAK (FIG. 7).

Figure 8:
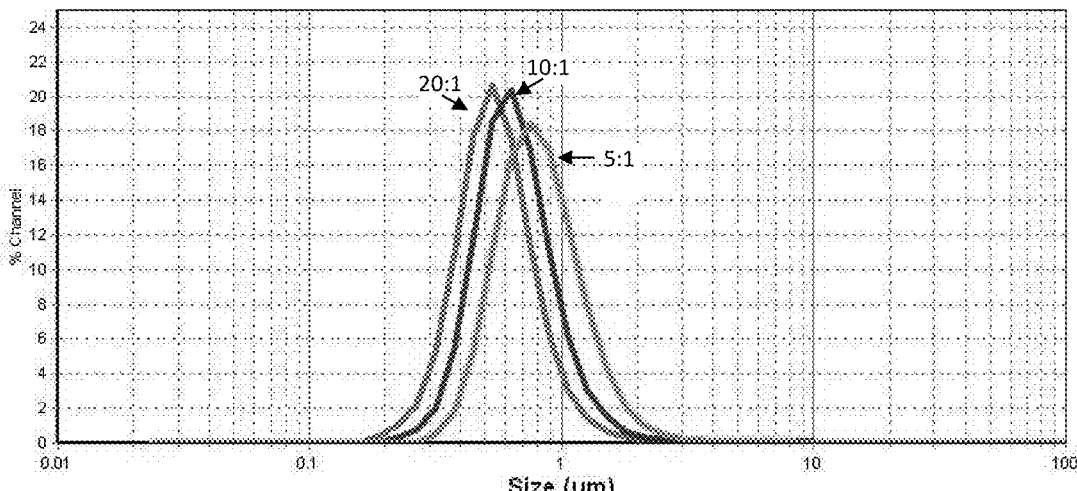
FIG. 8 shows particle size distribution of Bead Milled samples with varying LE:Poloxamer Ratios.

Additionally, the API: Surfactant ratio was studied. Samples were made containing 30% LE+0.714% Boric acid+Poloxamer 407 (Pluronic F127 surfactant) to obtain LE:Poloxamer ratios of 20:1, 10:1 and 5:1. The samples were milled with 0.5-mm $ZiO_2$ beads on a wrist shaker overnight. The results are summarized in FIG. 8. The lower poloxamer concentration showed better results than the higher concentrations (noting this contradicts information from a literature article (Liu et al., "Nanosuspensions of poorly soluble drugs: preparation and development by wet milling", Int. J. of Pharm 411 (1-2): 215-222, 2011).

Figure 9:
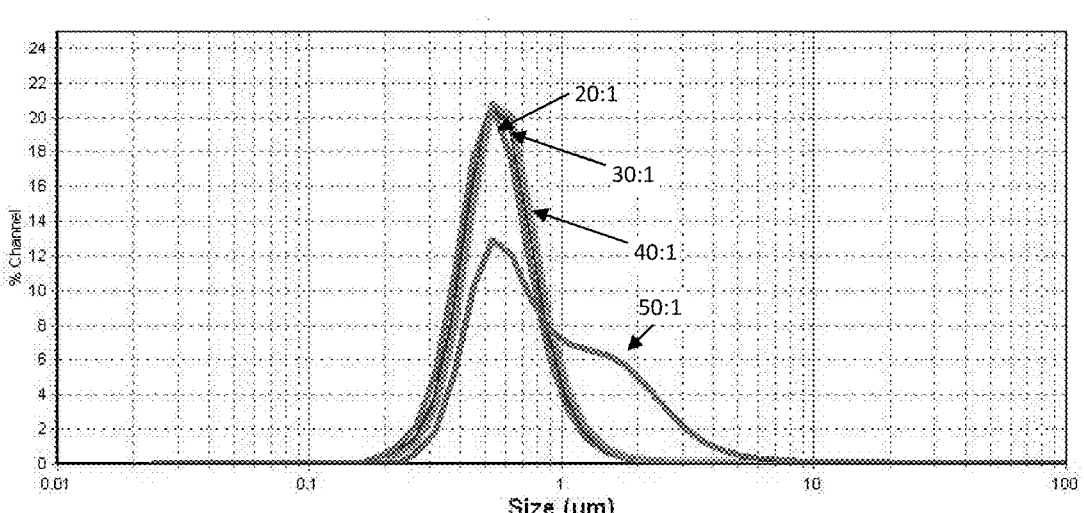
FIG. 9 shows particle size distribution of Bead Milled samples with varying LE:Poloxamer Ratios.
Figure 10:
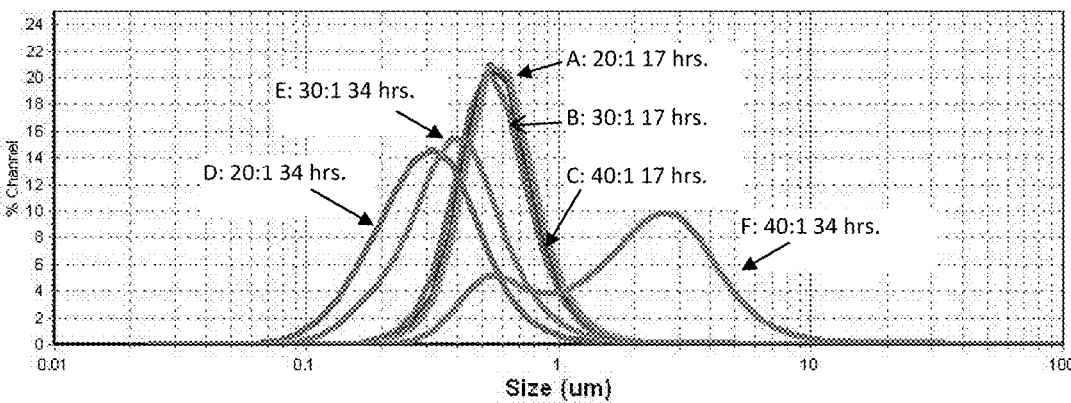
FIG. 10 shows particle size distribution of Bead Milled samples at 17 hours vs. 34 hours.
Figure 11:
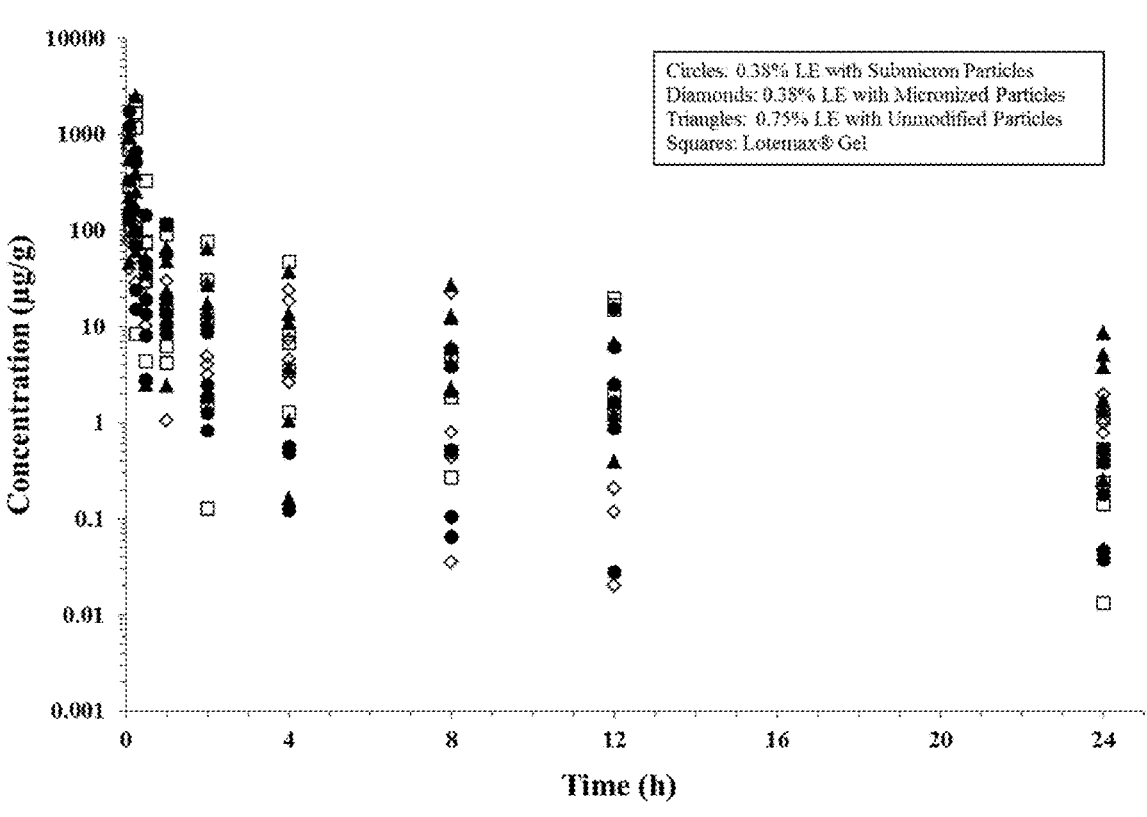
FIG. 11 shows Individual LE Concentrations in Tear Fluid after a Single Topical Ocular Administration to Dutch Belted Rabbits.
Figure 12:
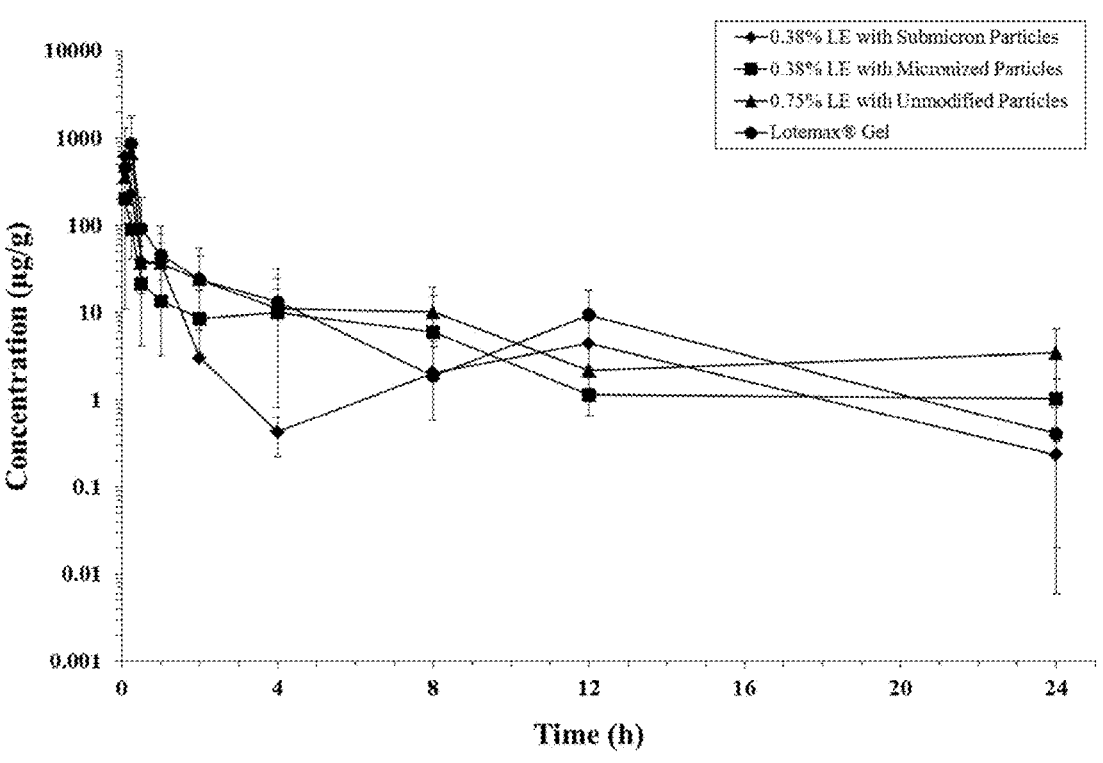
FIG. 12 shows Mean (±SD) LE Concentrations in Tear Fluid after a Single Topical Ocular Administration to Dutch Belted Rabbits.
Figure 13:
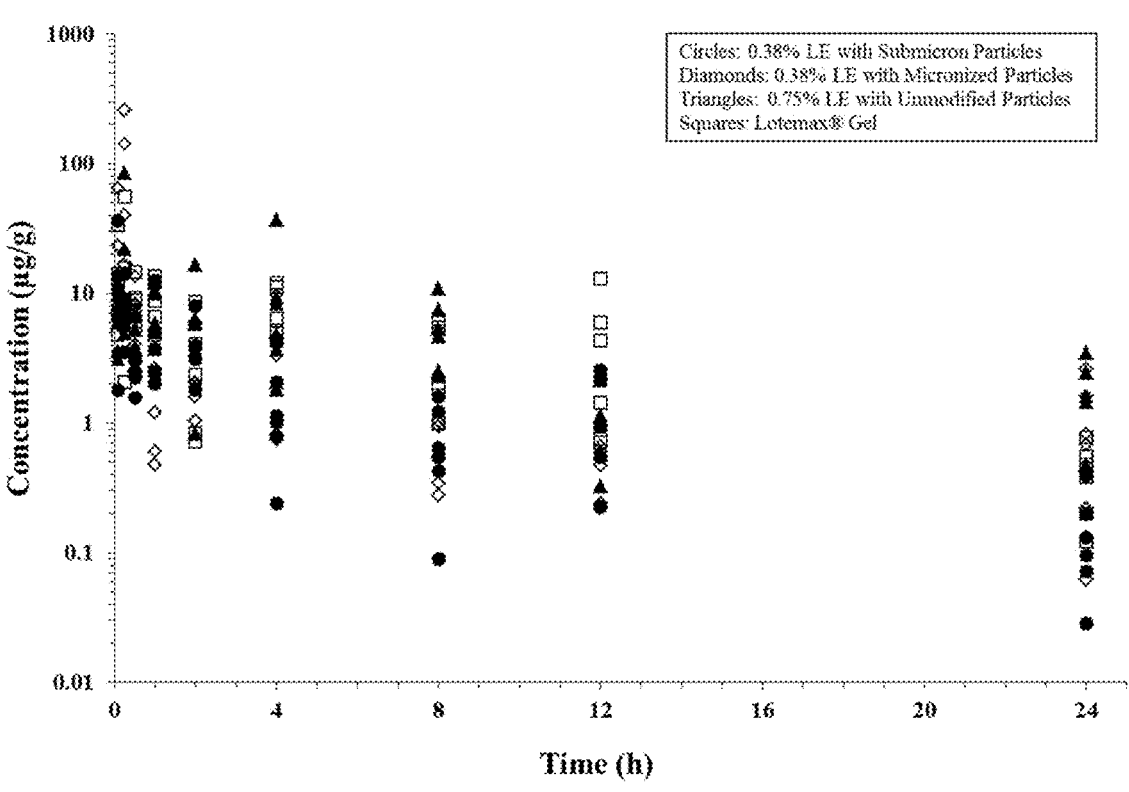
FIG. 13 shows Individual LE Concentrations in Bulbar Conjunctiva after a Single Topical Ocular Administration to Dutch Belted Rabbits.
Figure 14:
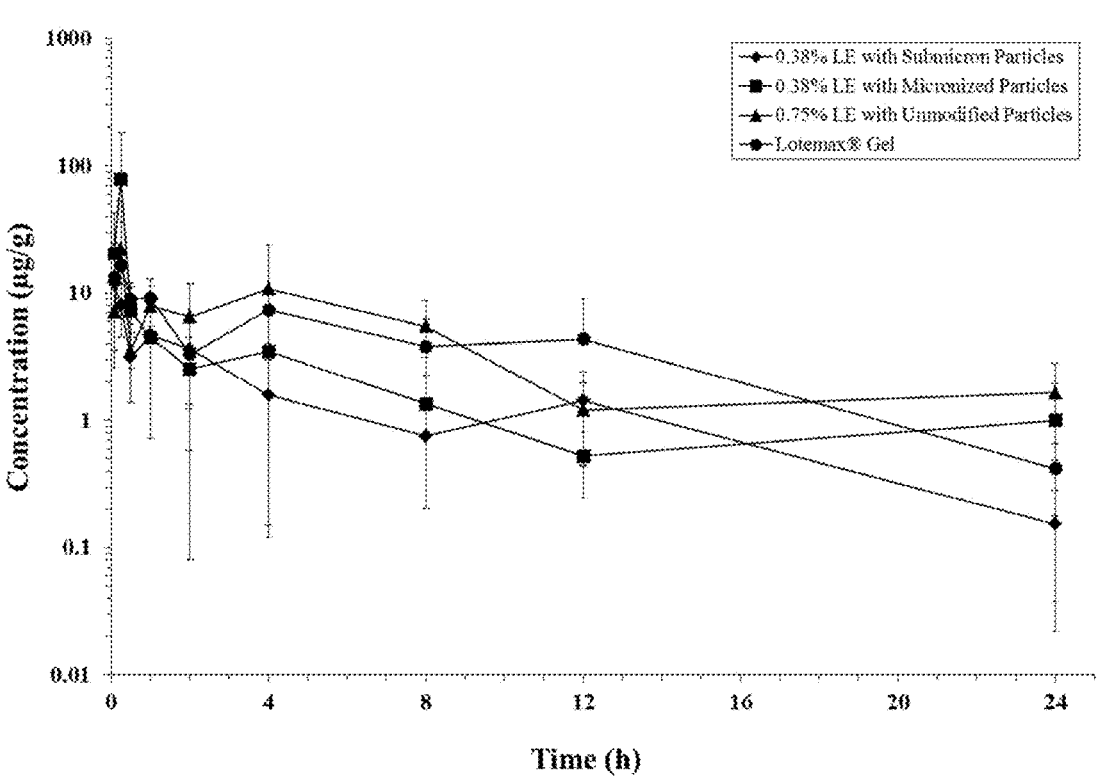
FIG. 14 shows Mean (±SD) LE Concentrations in Bulbar Conjunctiva after a Single Topical Ocular Administration to Dutch Belted Rabbits.
Figure 15:
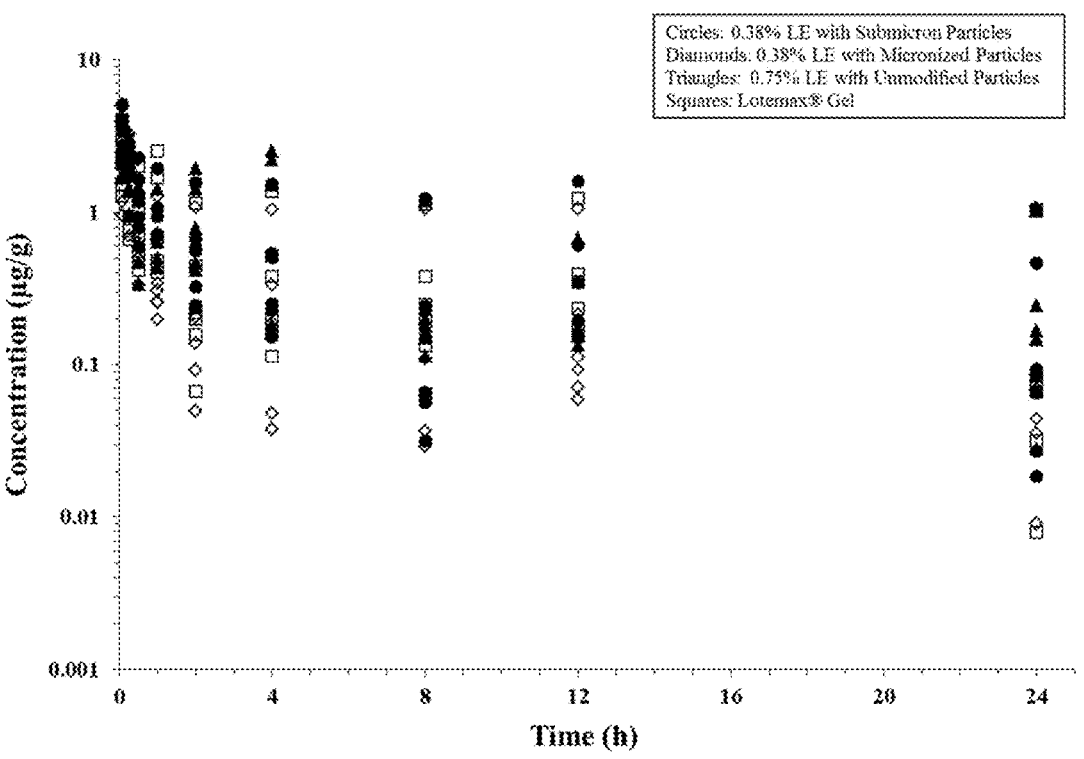
FIG. 15 shows Individual LE Concentrations in Cornea after a Single Topical Ocular Administration to Dutch Belted Rabbits.
Figure 16:
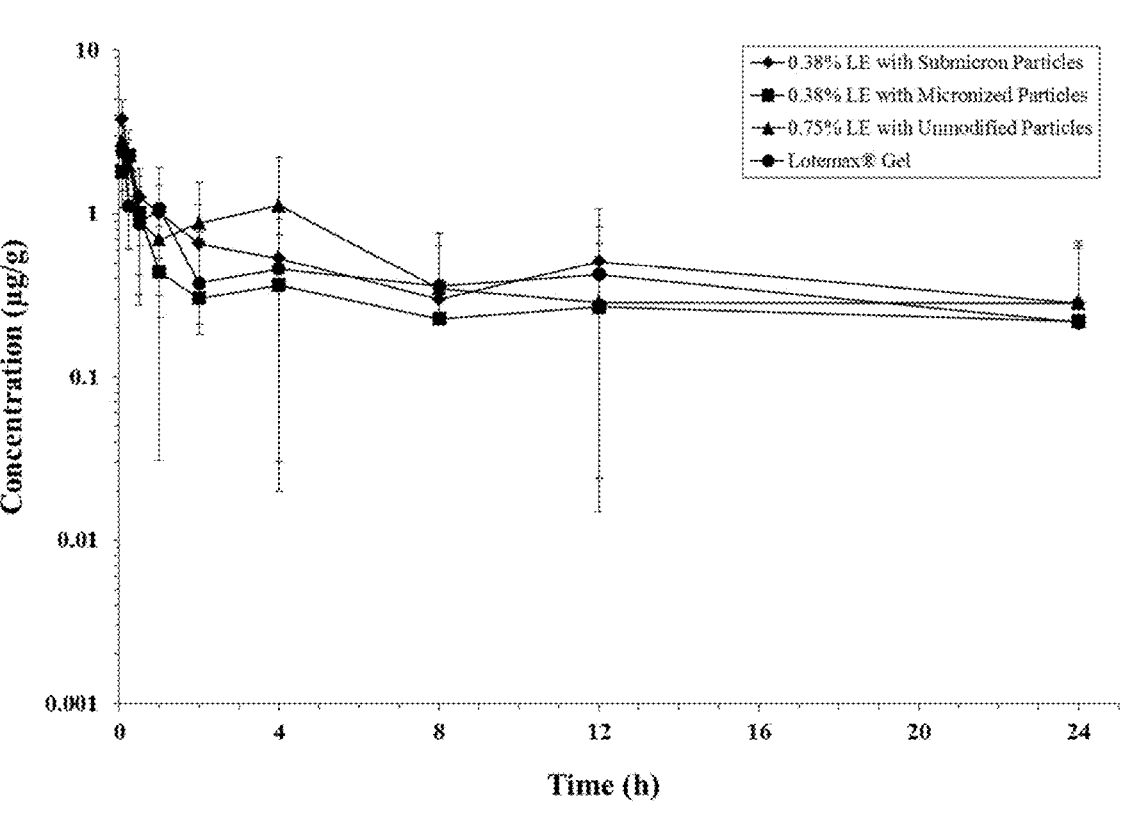
FIG. 16 shows Mean (±SD) LE Concentrations in Cornea after a Single Topical Ocular Administration to Dutch Belted Rabbits.
Figure 17:
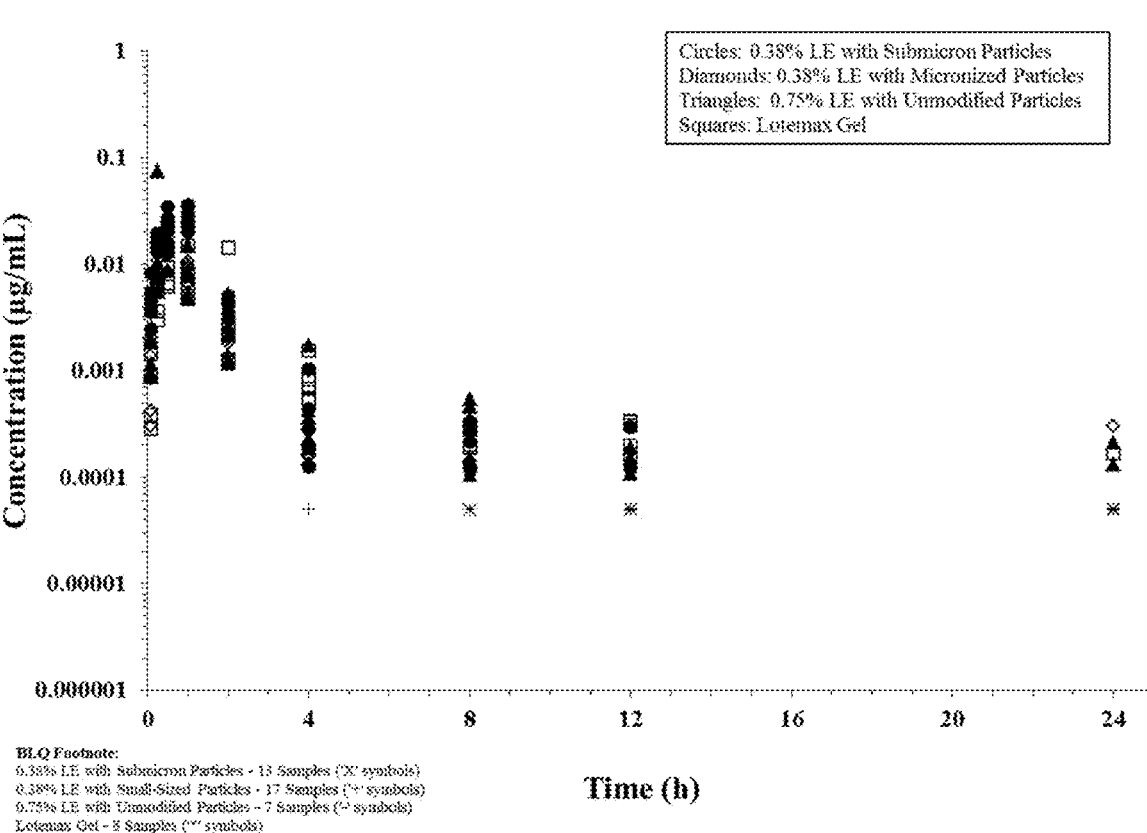
FIG. 17 shows Individual LE Concentrations in Aqueous Humor after a Single Topical Ocular Administration to Dutch Belted Rabbits
Figure 18:
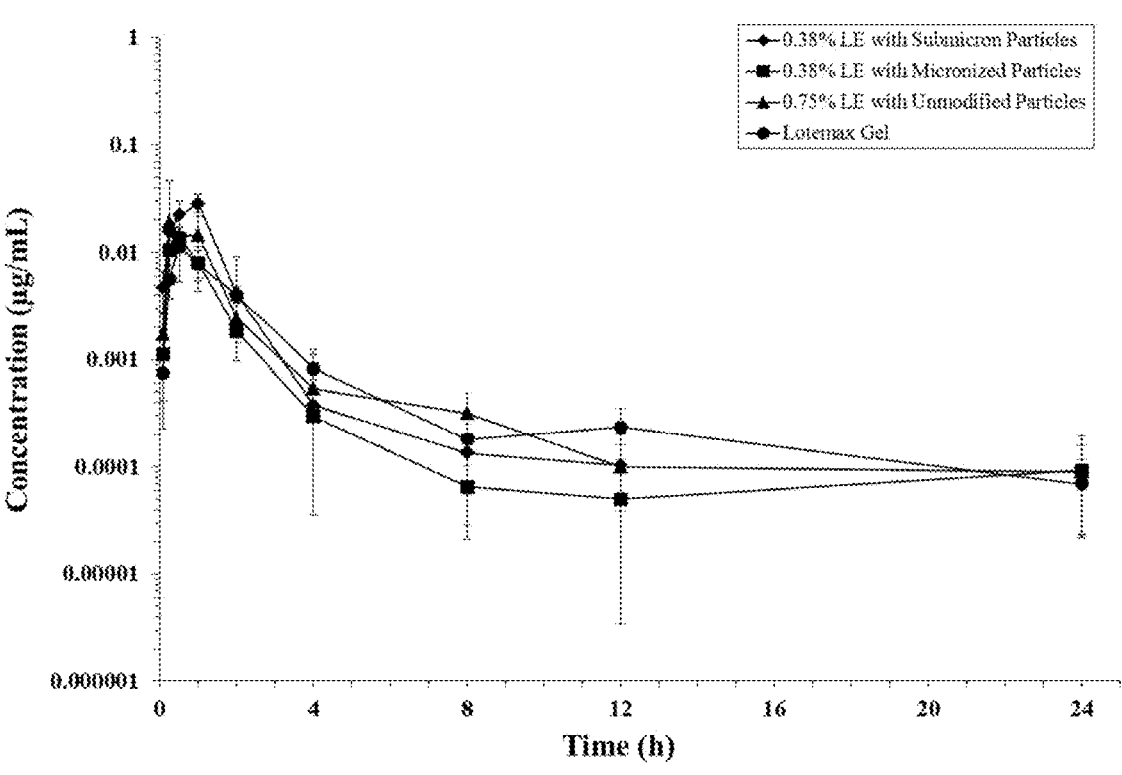
FIG. 18 shows Mean (±SD) LE Concentrations in Aqueous Humor after a Single Topical Ocular Administration to Dutch Belted Rabbits.
Figure 19:
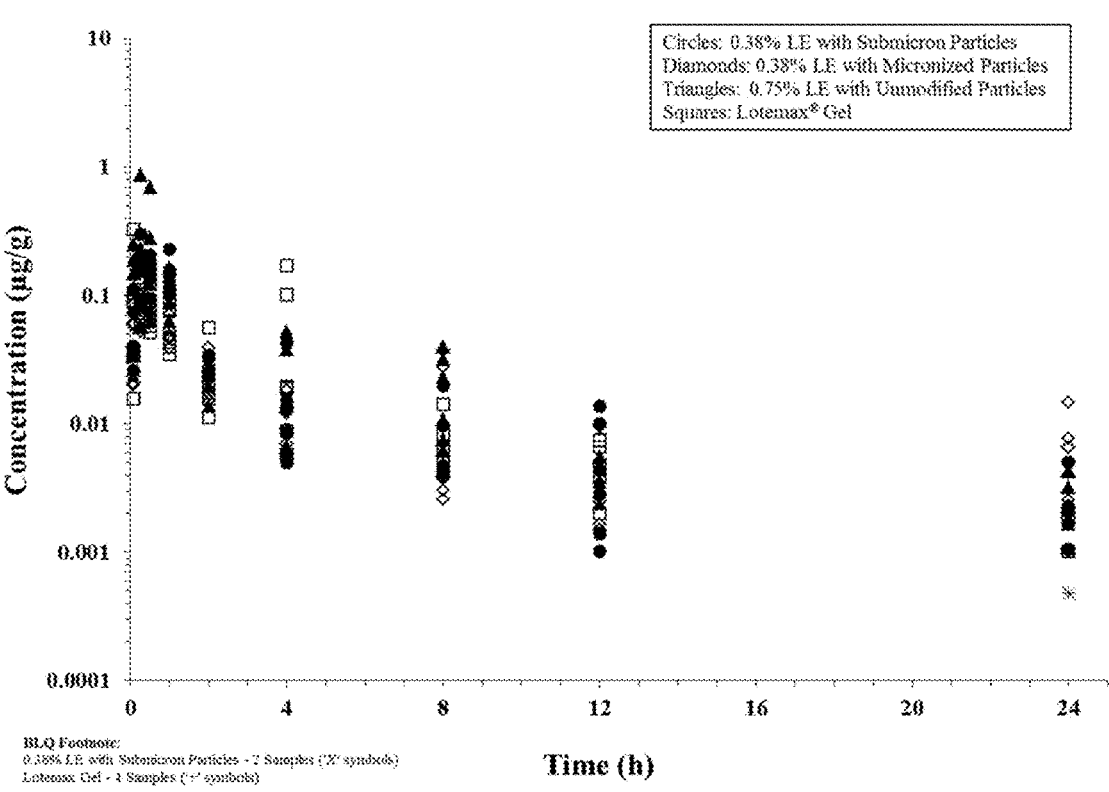
FIG. 19 shows Individual LE Concentrations in Iris/Ciliary Body after a Single Topical Ocular Administration to Dutch Belted Rabbits.
Figure 20:
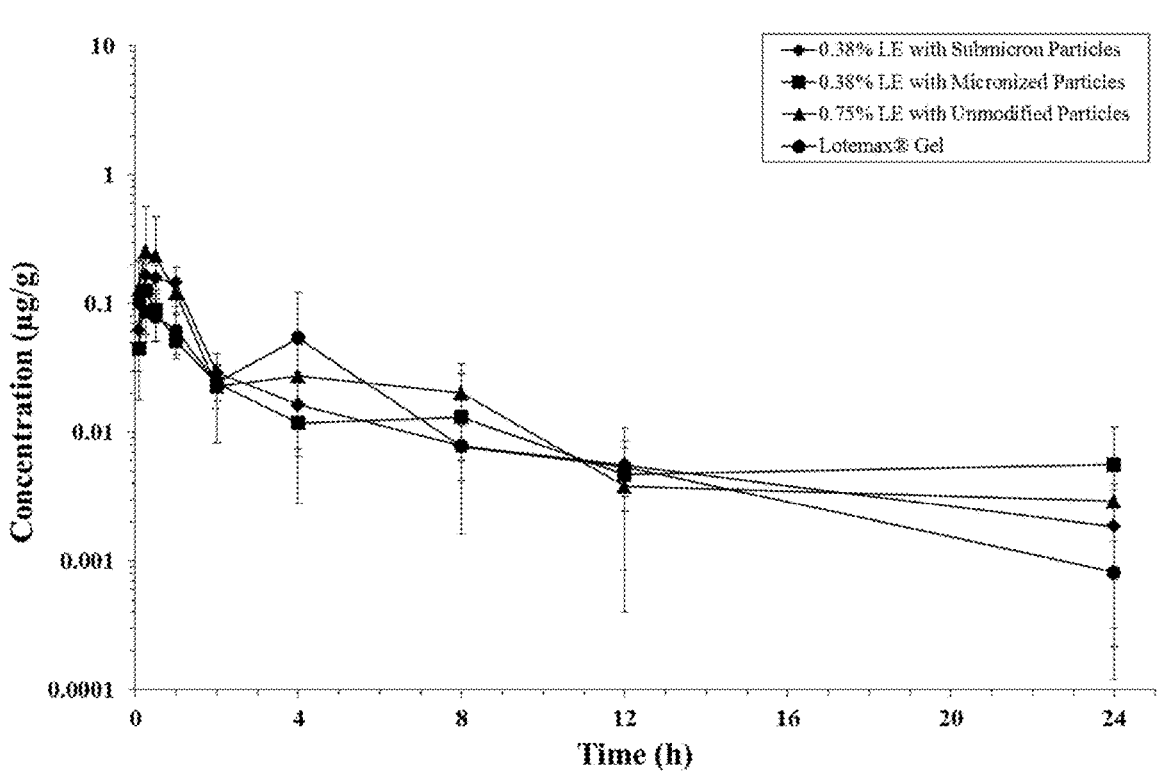
FIG. 20 shows Mean (±SD) LE Concentrations in Iris/Ciliary Body after a Single Topical Ocular Administration to Dutch Belted Rabbits.
Figure 21:
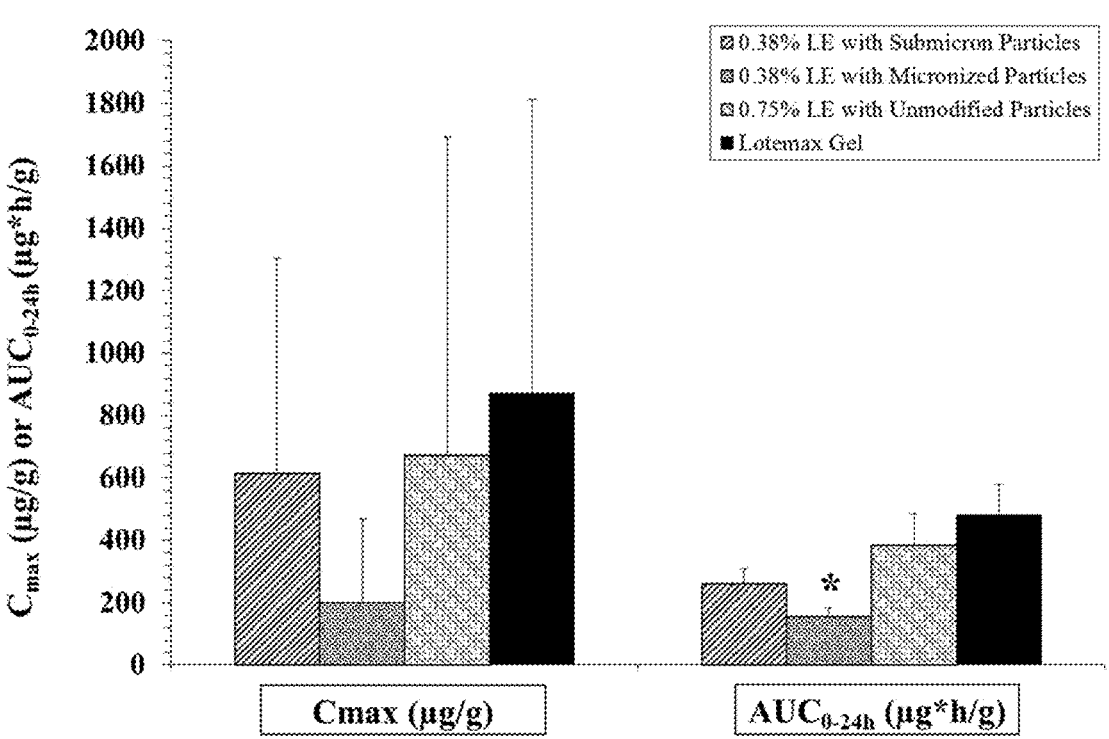
FIG. 21 shows Mean (±SD) $C_{max}$ and $AUC_{(0-24\ h)}$ (±SE) Values in Tear Fluid after a Single Topical Ocular Administration to Dutch Belted Rabbits.
Figure 22:
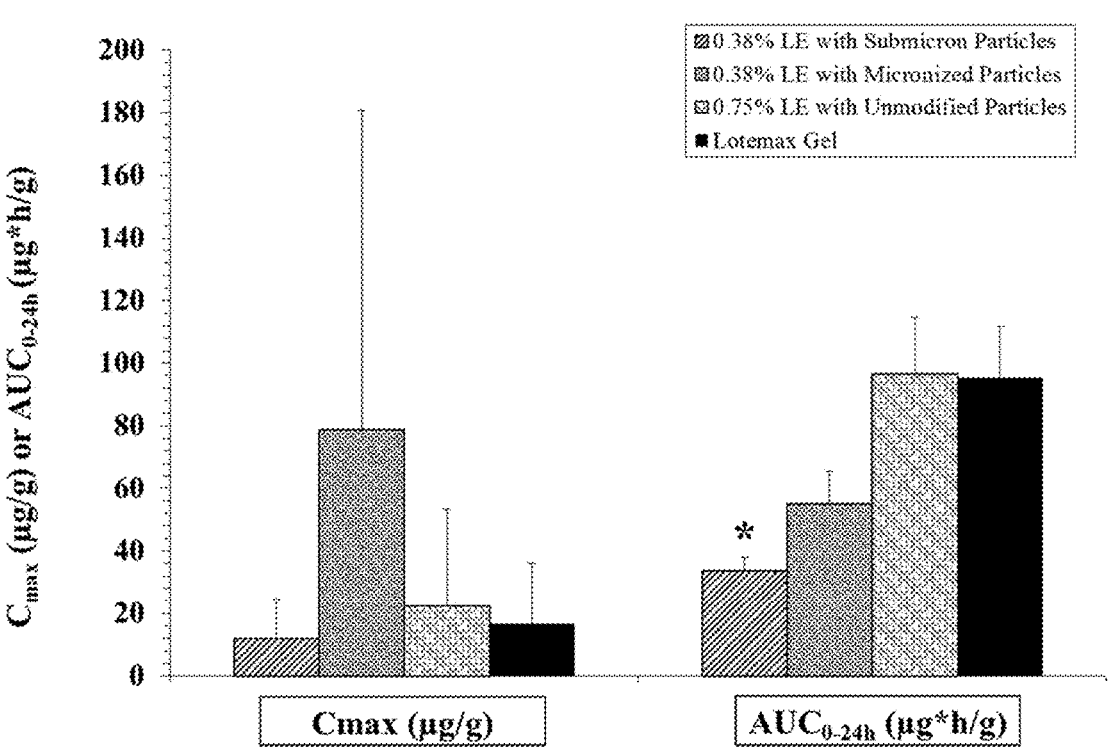
FIG. 22 shows Mean (±SD) $C_{max}$ and $AUC_{(0-24\ h)}$ (±SE) Values in Bulbar Conjunctiva after a Single Topical Ocular Administration to Dutch Belted Rabbits.
Figure 23:
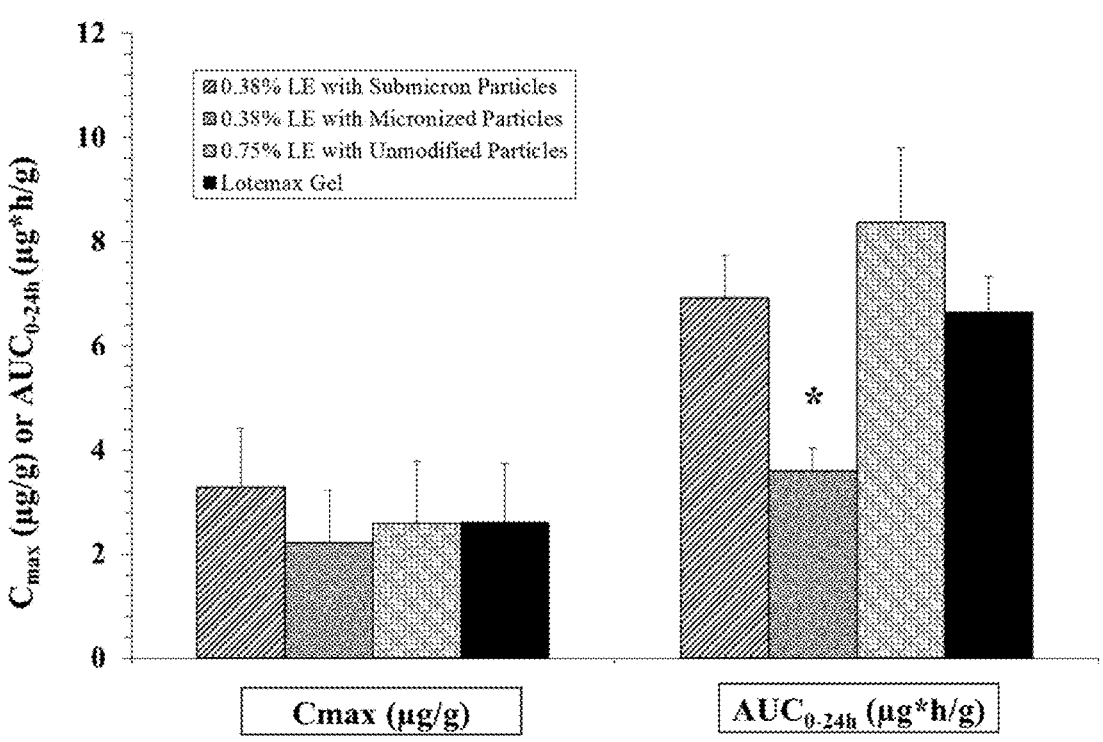
FIG. 23 shows Mean (±SD) $C_{max}$ and $AUC_{(0-24\ h)}$ (±SE) Values in Cornea after a Single Topical Ocular Administration to Dutch Belted Rabbits.
Figure 24:
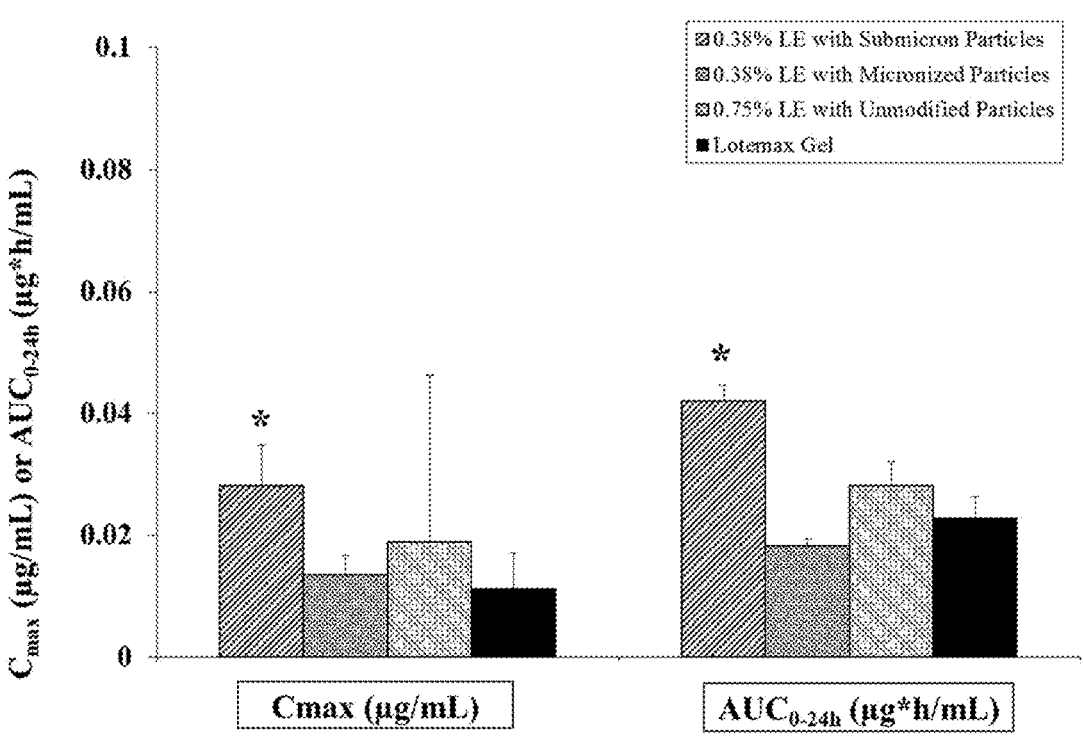
FIG. 24 shows Mean (±SD) $C_{max}$ and $AUC_{(0-24\ h)}$ (±SE) Values in Aqueous Humor after a Single Topical Ocular Administration to Dutch Belted Rabbits.
Figure 25:
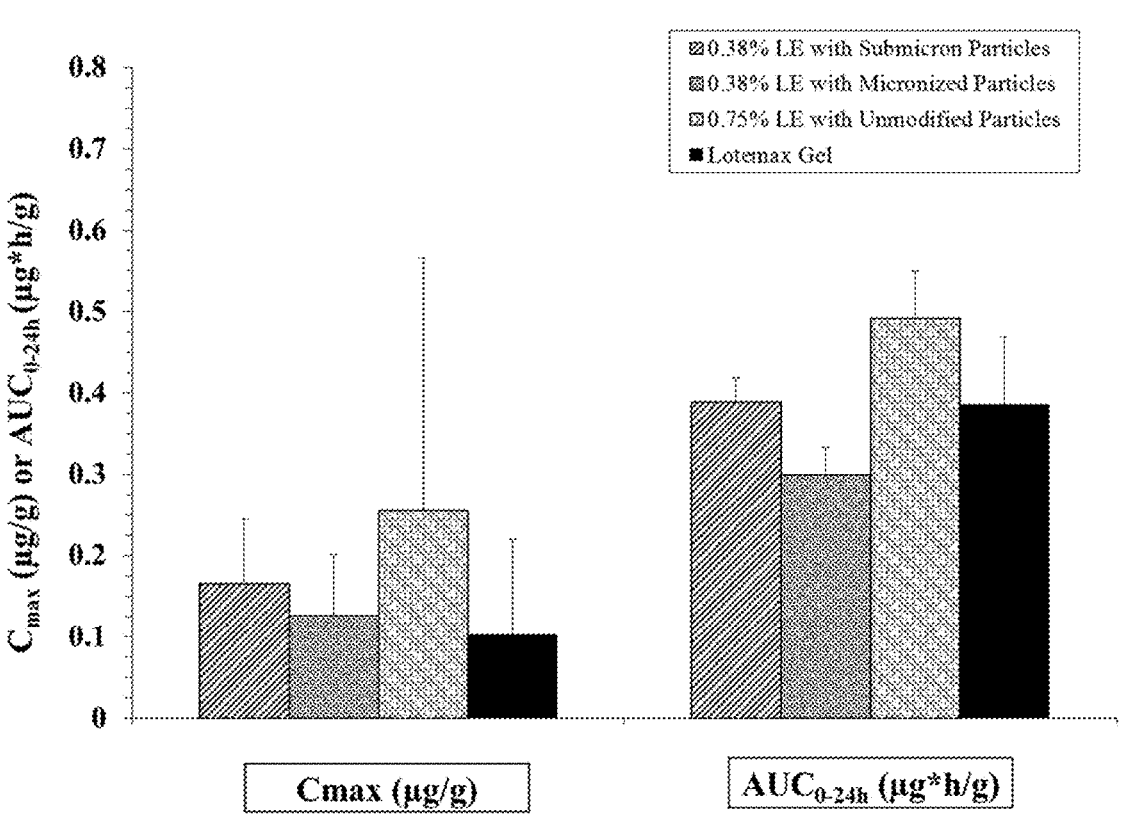
FIG. 25 shows Mean (±SD) $C_{max}$ and $AUC_{(0-24\ h)}$ (±SE) Values in Iris/Ciliary Body after a Single Topical Ocular Administration to Dutch Belted Rabbits.
Figure 36:
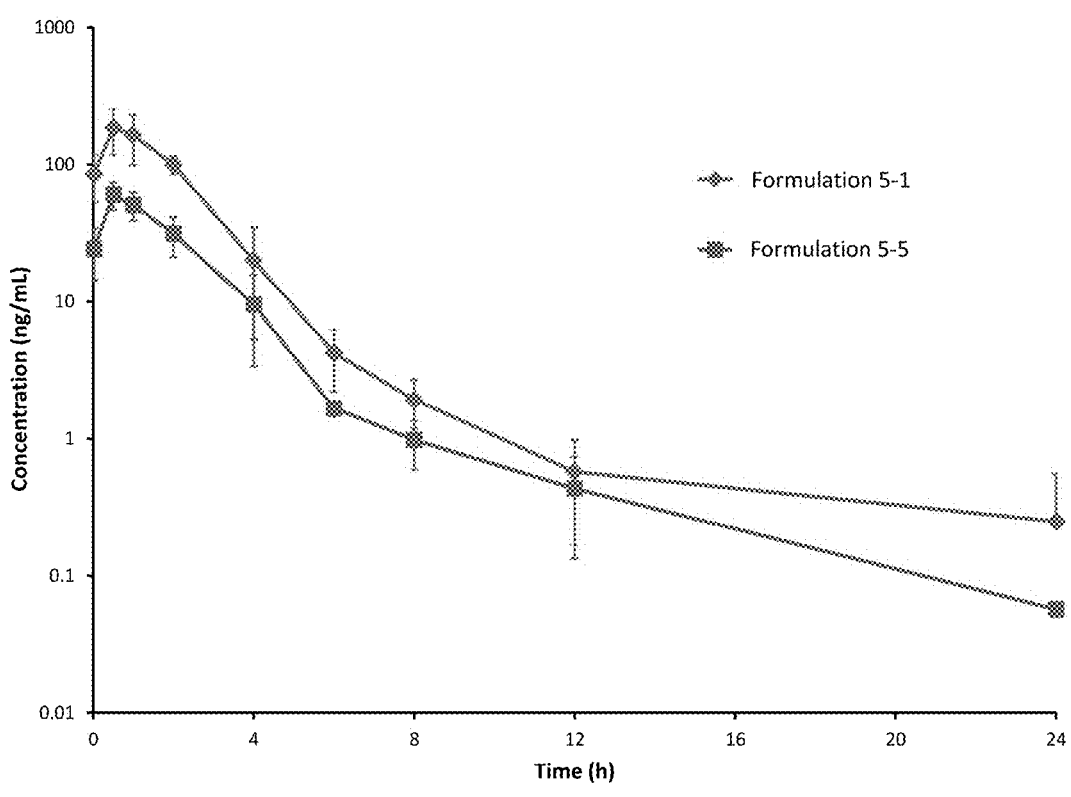
FIGS. 36 to 38 shows Difluprednate Metabolite Concentrations in Aqueous Humor after a Single Topical Ocular Administration of Difluprednate to Dutch Belted Rabbits
Figure 37:
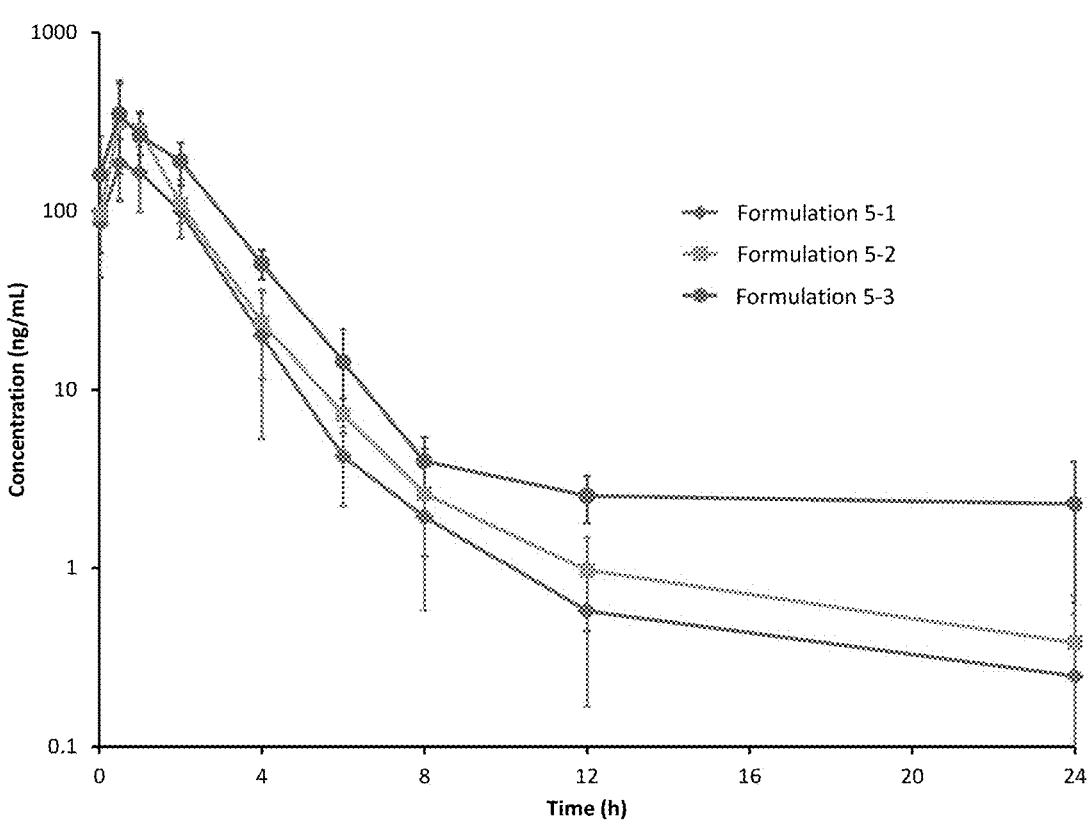
Figure 38:
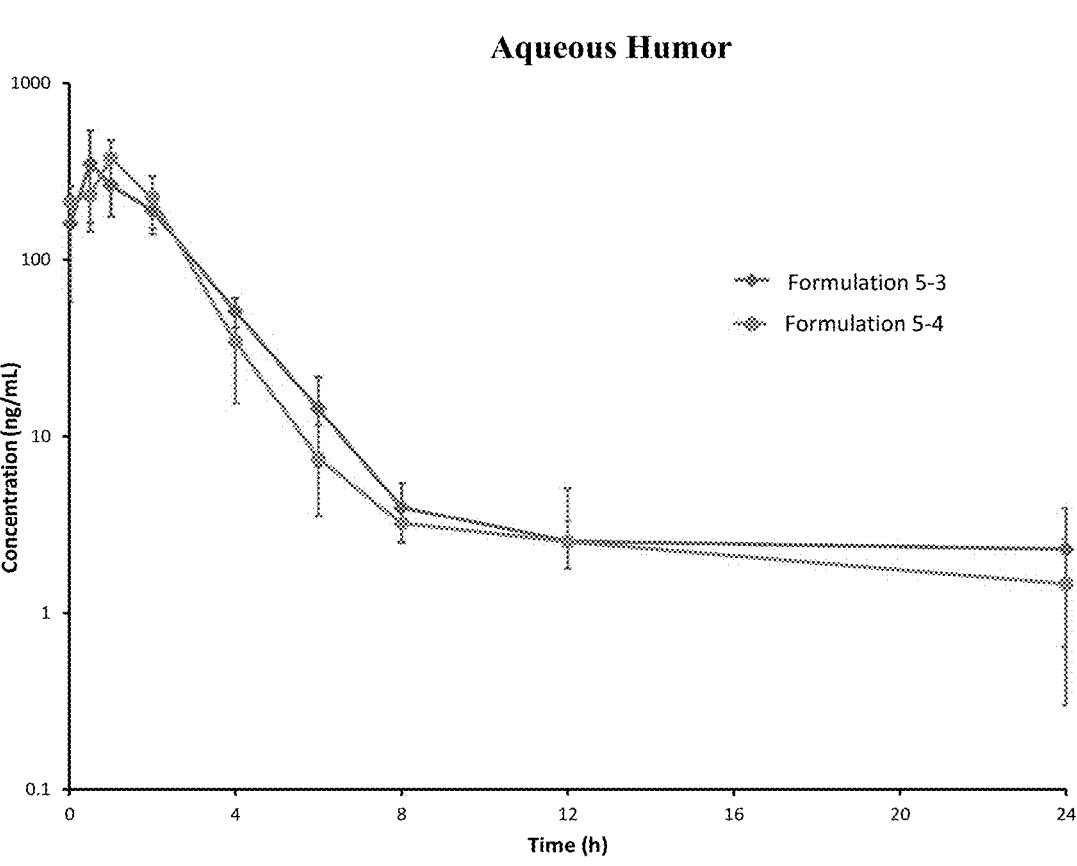
Figure 39:
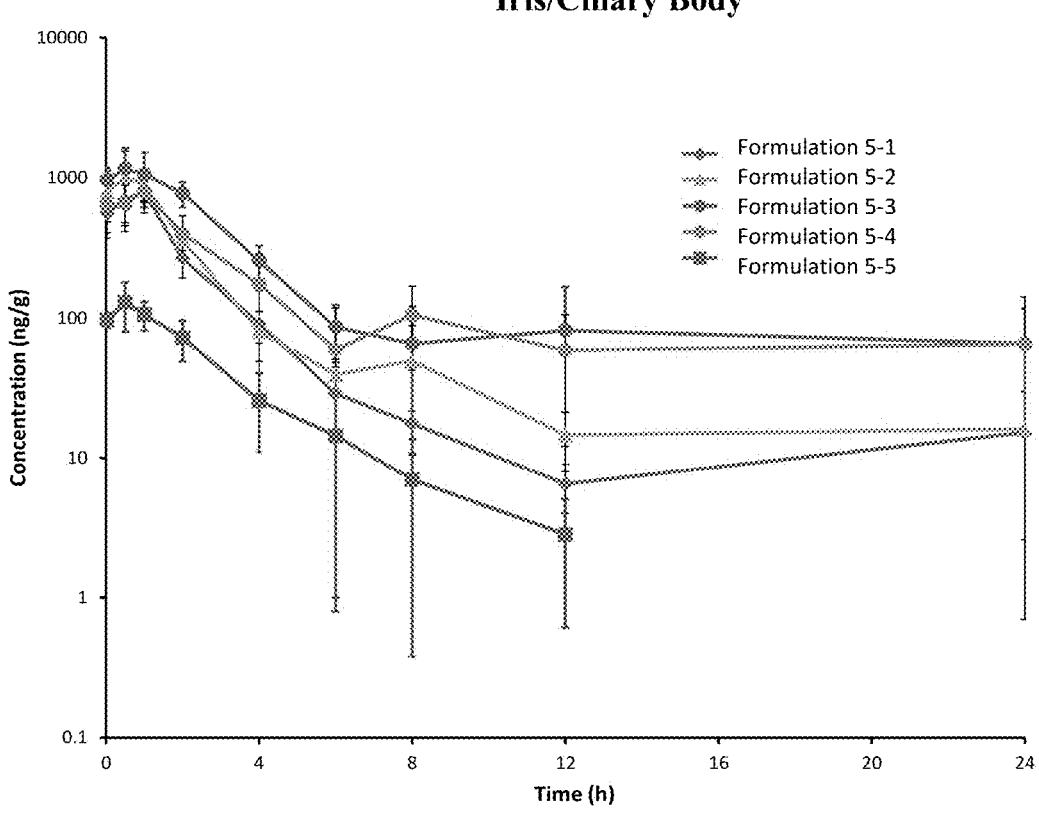
FIG. 39 shows Difluprednate Metabolite Concentrations in Iris/Ciliary after a Single Topical Ocular Administration of Difluprednate to Dutch Belted Rabbits
Figure 41:
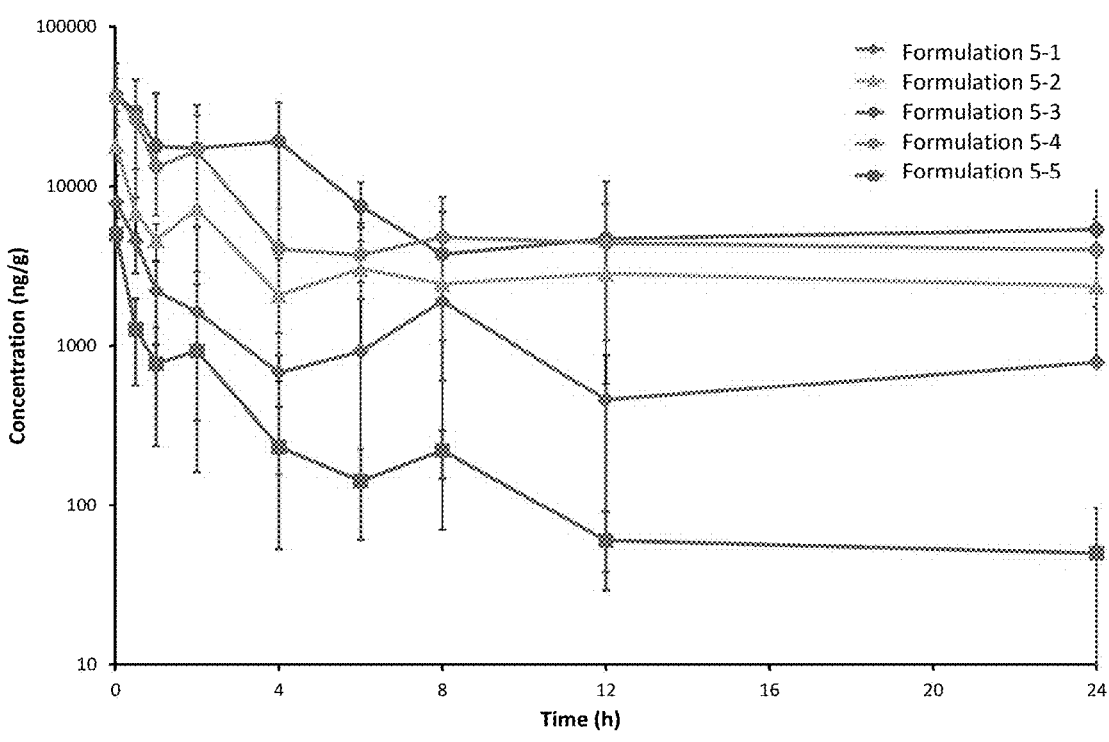
FIG. 41 shows Difluprednate Metabolite Concentrations in Bulbar Conjunctiva after a Single Topical Ocular Administration of Difluprednate to Dutch Belted Rabbits

Additional 30% LE samples were made using 30:1, 40:1 and 50:1 LE:Poloxamer ratios. The 20:1, 30:1 and 40:1 samples showed similar particles sizes after 17 hours of milling (FIG. 9). These three samples were then milled for an additional 17 hours. After a total of 34 hours milling, the 40:1 sample became larger and bimodal possibly due to an insufficient amount of surfactant for the increase in surface area of the LE. Both the 30:1 and 20:1 samples continued to get smaller over time, with the 20:1 sample obtaining the smallest particle size (FIG. 10).

Example 2—Stabilization of Polycarbophil Formulation

The present inventors recognized that sub-micron particles of LE in a polycarbophil formulation are not physically stable and tend to aggregate over time. It is believed the polycarbophil polymer forms an open mesh type of structure that produces a shear thinning gel but allows unimpeded movement of particles within the matrix. In contrast, hydroxypropylmethyl cellulose (HPMC) forms a more compact structure that can enhance the viscosity within the polycarbophil matrix reducing particle movement. Also, HPMC inhibits nucleation stabilizing small particles by reducing the Oswald ripening effect. Accordingly, this study was designed to understand the contribution of viscosity enhancement and nucleation inhibition on the stabilizing property of hydroxypropylmethyl cellulose (HPMC), especially HPMC E4M, and other potential stabilizers.

Various samples of 0.38% LE gel were made employing polycarbophil along with 0.25% HPMC E4M or other stabilizers. Slurries were bead-milled as in Example 1. These samples were then placed in glass vials and incubated at 25° C. and 40° C. At various time points the samples were removed and tested for particle size by the light diffraction technique. The particle sizes after 8.5 months, stored at 40° C., are reported in Table 2: VMD denotes volume mean diameter, and $D_{v95}$ denotes the particle diameter below which particles having 95% of the cumulative volume of all particles fall. Table 2 summarizes the stabilizers that functioned to enhance viscosity and/or inhibit nucleation.

TABLE 2

| | Stabilizer | Viscosity Enhancer | Nucleation inhibitor | VMD | Dv95 |
|---|---|---|---|---|---|
| P | 0.25% HPMC E4M | X | X | 0.94 | 3.99 |
| P | 0.15% HPMC E4M | X | X | 0.87 | 3.23 |
| MP | 0.05% HPMC E4M | X | X | 1.23 | 3.48 |
| NP | 0.0006% HPMC E4M | X | X | 2.68 | 12.33 |
| NP | No Stabilizer | | | 3.45 | 22.24 |
| MP | 0.25% HPMC E3LV | | X | 1.15 | 3.62 |
| NP | 0.25% CMC | X | | 3.33 | 19.47 |
| NP | 0.25% PVP | X | | 3.89 | 29.23 |
| P | 0.25% Soluplus | | X | 0.83 | 3.61 |

P = Protected
MP = Moderately Protected
NP = Unprotected

15

Titration of HPMC E4M shows a minimum critical concentration of approximately 0.05% was needed to stabilize the sub-micron LE particles. The HPMC E3LV sample has similar nucleation inhibition properties as HPMC E4M but provides lower viscosity enhancement, and shows moderate protection similar to the 0.05% HPMC E4M sample. The polyvinyl pyrrolidinone (PVP) sample provides viscosity enhancement and exhibits results similar to the no-stabilizer sample. Carboxymethyl cellulose (CMC) is a known suspending agent providing both viscosity enhancement and surface activity. The grade used here has low viscosity. This sample also exhibits results similar to the no-stabilizer sample. Soluplus™ stabilizer (available from BASF), containing a polyvinyl caprolactam-polyvinyl acetate-polyethylene glycol graft copolymer, is a strong nucleation inhibitor with no viscosity enhancement. This sample shows stability similar to the 0.25% HPMC E4M sample.

This study shows the ideal combination of viscosity enhancement and nucleation inhibition was provided by HPMC, especially grade E4M, and this supplemental suspending agent was effective to stabilize the sub-micron particles.

Example 3—Rheology Study

The effectiveness of topical corticosteroids can be limited by their dissolution and residence time on the ocular surface. This study examined the dissolution and viscoelastic characteristics of Composition A (containing submicron LE particles, 0.38%) as compared to commercial LE gel, Lotemax® Ophthalmic Gel, 0.5%.

Yield stress and oscillatory rheology measurements were performed using a TA Instruments rheometer fitted with a vane rotor and cup containing 40 g undiluted product at 25° C. Dissolution of LE submicron particles (0.6-μm diameter) and LE micronized particles (3-μm diameter used in Lotemax® Ophthalmic Gel, 0.5%) was measured at 200% of saturation in PBS/0.45% SDS using a VanKel dissolution tester. Dissolution was also determined in a flow-through assay simulating tear flow on the eye. An 8-mL LE submicron or micronized suspension was mixed with 3 mL of PBS/3.75% BAK. PBS/3.75% BAK was then flowed through the diluted LE suspension at 10 mL/min. Samples were taken from the outflow and the amount of dissolved LE was determined by HPLC. This method simulates an 11-μL tear volume with a flow rate of 10 μL/min.

Rheology analysis of submicron LE gel 0.38% shows a yield stress of approximately 4 Pa, confirming the gel structure is similar to Lotemax® Ophthalmic Gel, 0.5%. There was a 2.6-fold increase in dissolution with the submicron LE (0.38%) as compared to micron LE (0.5%) at 30 sec. The 0.38% submicron sample reached saturation at approximately 1.5 minutes compared to approximately 5 minutes for the 0.5 micronized sample. In the flow-through model there was an increase in dissolution over a longer time period for the submicron vs. micronized LE. Comparison of the AUC of the concentration vs. time curve at increasing drug concentration indicated that there was a 1.3 fold increase overall in the rate of dissolution with the 0.38% submicron vs. the 0.5% micronized formulation.

Accordingly, the submicron LE gel, 0.38% (Composition A) has similar viscoelastic characteristics as Lotemax® Ophthalmic Gel 0.5%, and therefore was expected to be storage-stable, non-settling, and provide uniform drug delivery from the container.

Example 4—Investigation of the Effect of Particle Size and Concentration on the Ocular Pharmacokinetics of Loteprednol Etabonate Following a Single Topical Ocular Administration to Dutch Belted Rabbits The purpose of this study was to assess the effect of particle size on the ocular pharmacokinetics (PK) of loteprednol etabonate (LE) following a single topical ocular administration to Dutch Belted rabbits, and determine if a higher concentration of LE provides increased ocular exposure. Lotemax® Gel (Loteprednol etabonate 0.5% ophthalmic gel) (LE) is a potent corticosteroid in a polycarbophil-based gel formulation approved for the treatment of post-operative pain and inflammation following ocular surgery. This investigation was designed to evaluate the effect of reduced particle size on the ocular PK of LE following a single, topical ocular administration to Dutch Belted rabbits. A third formulation that contained the same sized particles of LE as the commercial formulation but at a higher concentration was also evaluated to determine if a higher dose of LE provides increased ocular exposure. Lotemax® Gel was used as the comparator formulation.

A total of 108 male Dutch Belted rabbits were used in this non-GLP, non-crossover pharmacokinetic study. The rabbits were approximately 7-8 months of age and weighing between 1.56-2.69 kg. Prior to the start of the study, animals were randomly assigned to one of four study groups. On the day of dosing, animals received a single 35-μL topical ocular dose containing the appropriate formulation into each eye.

Animals in Group 1 received a 0.38% gel formulation prepared with submicron-sized particles of LE (Formulation 1)

Animals in Group 2 received a 0.38% gel formulation that contained micronized particles of LE (Formulation 2)

Animals in Group 3 received a 0.75% gel formulation that had the same particle size as the current Lotemax® Gel product (Formulation 3).

Animals in Group 4 received the marketed product Lotemax® Gel (0.5%) (Formulation 4).

Animals were observed throughout the duration of the study for general health and appearance. At pre-determined time intervals after dosing, animals were euthanized and selected ocular tissue samples were collected. Concentrations of LE in ocular tissues were determined by LC/MS/MS. All in-life procedures were conducted at PharmOptima (Portage, MI). Bioanalysis of ocular tissue samples was conducted at Bausch+Lomb (Rochester, NY). The experimental formulations were prepared by Bausch+Lomb Formulations Development and shipped to the test site as ready to use materials. Lotemax® Gel was provided by Bausch+Lomb (Tampa, FL). Details of the test formulations are provided in Table 4-1.

TABLE 4-1

| | Formulation 1: Submicron Particle Size Lot #3463EP026-3 | Formulation 2: Micronized Particles Lot# 3463EP026-2 | Formulation 3: Unmodified Particle Size Lot# 3463EP026-1 | Formulation 4: Lotemax Gel Lot# 2420850307 |
|---|---|---|---|---|
| | Loteprednol Etabonate Formulation Summary Concentration (mg/mL)—Balance Water | | | |
| Component | | | | |
| Disodium EDTA | 0.55 | 0.55 | 0.55 | 0.55 |
| Sodium Chloride | 0.5 | 0.5 | 0.5 | 0.5 |
| Polycarbophil | 3.75 | 3.75 | 3.75 | 3.75 |
| Tyloxapol | 0.5 | 0.5 | 0.5 | 0.5 |
| BAK | 30 ppm | 30 ppm | 30 ppm | 30 ppm |
| Glycerin | 8.8 | 8.8 | 8.8 | 8.8 |
| Propylene Glycol | 4.4 | 4.4 | 4.4 | 4.4 |
| Boric Acid | 5.0 | 5.0 | 5.0 | 5.0 |
| Sodium Hydroxide | q.s. to pH 6.5 | q.s. to pH 6.5 | q.s. to pH 6.5 | q.s. to pH 6.5 |
| Loteprednol Etabonate | 3.90 | 3.96 | 7.44 | 5 |
| API Lot # | AAX-009A | EQ3011 lot 7289 | XA21010 lot 071279545 | 172121 |
| Particle Size ($Dv_{50}$) | 0.6 μm | 2.87 μm | 2.67 μm | 2.71 μm |

An ophthalmic examination was performed on both eyes of all study animals prior to shipment from the vendor to the test facility. The examination consisted of an evaluation of the anterior segment of the eye using a slit lamp binocular microscope to verify that there were no pre-existing ophthalmic abnormalities that would interfere with the outcome of the study. Upon arrival at the test facility, a visual examination was performed on all animals to confirm that they were in good health. Animals were then weighed and randomly assigned to one of four study groups of 27 animals each using a random number generator.

On the day of dosing, animals (fed) received a single, 35-μL topical ocular administration of the appropriate test formulation into each eye. Animals in Group 1 received a 0.38% gel formulation prepared with submicron-sized particles of LE (also referred to as Submicron Formulation and Formulation). Animals in Group 2 received a 0.38% gel formulation that contained micronized particles of LE (also referred to as Micronized Formulation and Formulation 2). Animals in Group 3 received a 0.75% gel formulation that had the same particle size as the current Lotemax Gel product (also referred to as Unmodified Formulation and Formulation 3), and animals in Group 4 received Lotemax® Gel (0.5%) (also referred to as Comparator and Formulation 4). The formulations were not shaken prior to administration. Doses were instilled into the lower conjunctival sac of each eye using a calibrated Gilson M-50 positive displacement pipette. Immediately after dosing, the eyelids were gently held closed for several seconds to facilitate even distribution of the test substance over the surface of the eye and to minimize runoff. Animals were observed throughout the duration of the study for general health and appearance.

At pre-determined time intervals after dosing, animals (n=3/group/collection time) were humanely euthanized by intravenous overdose of sodium pentobarbital and ocular tissues were collected from each eye. Tear fluid (collected using Schirmer tear strips), bulbar conjunctiva, and aqueous humor (collected using a needle and syringe) were collected in situ, while the cornea and iris/ciliary body were collected once the eyes had been enucleated and flash-frozen in liquid nitrogen. Ocular tissue samples were collected at 0.0833 (5 min), 0.25 (15 min), 0.5 (30 min), 1, 2, 4, 8, 12, and 24 hours after dosing. Ocular tissue samples were stored frozen until being shipped on dry ice to Bausch+Lomb facility. Upon arrival, the samples were maintained at or below −20° C. until bioanalysis.

Concentrations of LE in ocular tissues were determined by LC/MS/MS. For the purpose of calculating mean concentrations, a value of ½ the lower limit of quantitation (LLQ) was assigned to all samples with concentrations below the LLQ (BLQ). In addition, any sample with a measured concentration that was BLQ and at least 10-fold below the median concentration or more than 10-fold above the median concentration in the respective sample pool was considered an outlier, and not included in any calculations. Based on these criteria, 17 (~8%) tear fluid samples, 3 (~1%) bulbar conjunctiva samples, 2 (~1%) cornea samples, 3 (~1%) aqueous humor samples, and 1 (~0.5%) iris/ciliary body sample were determined to be outliers.

Pharmacokinetic analysis of the composite concentration vs. time data was performed using non-compartmental methods in WinNonlin Professional® (version 5.3, Pharsight Corporation, St. Louis, MO). Due to the destructive nature of the sampling regimen employed in this study, mean composite data were used in the PK analysis. Nominal sample collection times were used in the PK analysis. PK parameters including maximum concentration ($C_{max}$) and the time at which the maximum concentration was observed ($T_{max}$) were determined directly from the concentration vs. time profiles. The area under the concentration vs. time curve ($AUC_{(0-24\ h)}$) values and the corresponding standard error (SE) estimates were calculated using the linear trapezoid method in WinNonlin and/or Microsoft Excel (2010).

To determine if exposure to LE in ocular tissues following administration of the experimental formulations (Formulations 1-3) varied significantly from exposure obtained with the commercial product (Formulation 4), the ($AUC_{(0-24h)}$) and SE estimates were compared using Welch's t-test as demonstrated by Schoenwald (1987) and Tang-Liu and Burke (1988). Schoenwald R D, Harris R G, Turner D, et al. Ophthalmic bioequivalence of steroid/antibiotic combination formulations. *Biopharm Drug Dispos.* 1987; 8:527-548; Tang-Liu D D, Burke P J. The effect of azone on ocular levobunolol absorption: calculating the area under the curve and its standard error using tissue sampling compartments. *Pharm Res.* 1988; 5:238-241. A two-tailed Student's t-test was used to determine significant differences in $C_{max}$ after an F-test was used to determine equal or unequal variance between individual concentration values at $C_{max}$. Differences were considered statistically significant when the calculated P value was less than or equal to 0.05. All statistical calculations were performed using Microsoft Excel (2010).

The pharmacokinetic parameter values obtained for LE following a single bilateral topical ocular administration are presented in Table 4-2. Mean and individual concentration vs. time data are presented in FIGS. 11 through 25, where BLQ denotes below level of quantification. In FIGS. 21-24, the asterisk (*) denotes statistically significant (p≤0.05) from Lotemax® Gel 0.5% LE. A summary of mean and individual concentration vs. time data is presented in FIGS. 26-35; in these figures, the superscript (a) denotes an apparent outlier, individual result differed by >10-fold from other results at this collection time, so value was not included in calculations. In FIGS. 33 and 34, a superscript (b) denotes a result below the lower limit of quantitation, so the value equal to ½ the value of the LLQ was assigned for the purpose of calculating summary statistics.

A total of 1080 ocular tissue samples were successfully analyzed in 6 bioanalytical runs. Samples consisted of tear fluid, bulbar conjunctiva, cornea, aqueous humor, and iris/ciliary body. A variable amount of 1:1 acetonitrile:water was added to the tear fluid, bulbar conjunctiva, cornea, and iris/ciliary body samples using a Tecan Freedom EVO 150. The volume of solvent was adjusted for each sample based on the individual sample weight to ensure a constant matrix concentration for all samples, standards, and quality control samples. All samples were sonicated and vortexed prior to transferring an aliquot to a 96-well sample plate. All samples above the HLQ were diluted 100× with 1:1 acetonitrile:water. Two sets of at least 8 standards and 3 quality controls (low, mid, and high, in triplicate) along with two 'zero' samples (blank matrix with internal standard) and 5 control blanks (blank matrix) were included in each bioanalytical run.

TABLE 4-2

Pharmacokinetic Parameter Values for Loteprednol Etabonate
Following a Single Topical Ocular Administration to Dutch Belted Rabbits

| Dose Group | Tissue/Matrix | $C_{max}$ (µg/g) | $T_{max}$ (h) | $AUC_{(0-24\ h)}$ (µg*h/g) |
|---|---|---|---|---|
| Group 1: | Tear fluid | 614 ± 691 | 0.0833 | 260 ± 49.2 |
| Submicron | Bulbar Conjunctiva | 12.0 ± 12.7 | 0.0833 | 33.5 ± 4.30 |
| Formulation | Cornea | 3.29 ± 1.13 | 0.0833 | 6.93 ± 0.798 |
| 0.38% | Aqueous Humor | 0.0281 ± 0.00665 | 1 | 0.0421 ± 0.00247[a] |
| (3.8 mg/mL) | Iris/Ciliary Body | 0.165 ± 0.0793 | 0.25 | 0.338 ± 0.0314 |
| (133 µg/eye) | | | | |
| Group 2: | Tear fluid | 201 ± 269 | 0.0833 | 157 ± 26.4 |
| Micronized | Bulbar Conjunctiva | 78.7 ± 102 | 0.25 | 55.0 ± 10.6 |
| Formulation | Cornea | 2.22 ± 1.01 | 0.25 | 3.61 ± 0.436 |
| 0.38% | Aqueous Humor | 0.0135 ± 0.00313 | 0.5 | 0.0183 ± 0.00107 |
| (3.8 mg/mL) | Iris/Ciliary Body | 0.126 ± 0.0758 | 0.25 | 0.299 ± 0.0335 |
| (133 µg/eye) | | | | |
| Group 3: | Tear fluid | 673 ± 1020 | 0.25 | 384 ± 101[a] |
| Unmodified | Bulbar Conjunctiva | 22.4 ± 31.0 | 0.25 | 96.6 ± 18.0 |
| Formulation | Cornea | 2.59 ± 1.20 | 0.0833 | 8.38 ± 1.43 |
| 0.75% | Aqueous Humor | 0.0190 ± 0.0273 | 0.25 | 0.0282 ± 0.00382 |
| (7.5 mg/mL) | Iris/Ciliary Body | 0.255 ± 0.311 | 0.25 | 0.491 ± 0.0586 |
| (262.5 µg/eye) | | | | |
| Group 4: | Tear fluid | 871 ± 942 | 0.25 | 483 ± 96.6[a] |
| Lotemax Gel | Bulbar Conjunctiva | 16.4 ± 19.7 | 0.25 | 95.0 ± 16.7 |
| 0.5% | Cornea | 2.61 ± 1.13 | 0.0833 | 6.66 ± 0.672 |
| (5 mg/mL) | Aqueous Humor | 0.0112 ± 0.00586 | 0.5 | 0.0228 ± 0.00349 |
| (175 µg/eye) | Iris/Ciliary Body | 0.102 ± 0.118 | 0.0833 | 0.385 ± 0.0841 |

$C_{max}$: Maximum mean (±SD) concentration observed after dosing; $T_{max}$: time $C_{max}$ was observed; $AUC_{(0-24\ h)}$: Mean (±SE) area under the concentration versus time curve from the time of dosing through 24 hours.
[a]AUC and/or standard error (SE) estimates calculated in Excel (reported) vary slightly from values obtained in WinNonlin due to rounding differences.
Note:
For aqueous humor, the relevant units for $C_{max}$ and AUC are µg/mL and µg*h/mL, respectively.

$C_{max}$: Maximum mean (±SD) concentration observed after dosing; $T_{max}$: time $C_{max}$ was observed; $AUC_{(0-24h)}$: Mean (±SE) area under the concentration versus time curve from the time of dosing through 24 hours.

([a]) AUC and/or standard error (SE) estimates calculated in Excel (reported) vary slightly from values obtained in WinNonlin due to rounding differences.

Note: For aqueous humor, the relevant units for $C_{max}$ and AUC are µg/mL and µg*h/mL, respectively.

Bioanalytical Method Summary—The LC/MS/MS methods for the quantitation of loteprednol etabonate (LE) in Dutch Belted rabbit ocular tissues were developed at Bausch+Lomb. The methods were assessed for precision and accuracy, but were not fully validated or GLP-compliant. Overall, the performance of the analytical methods was deemed acceptable to support this nonclinical PK study.

A summary of the bioanalytical range for Dutch Belted rabbit ocular tissues is provided in Table 4-3.

TABLE 4-3

Bioanalytical Range Summary

| Matrix | Ave. Tissue Weight (mg) | Assay Range of Standard Curve[a] | LLQ[b] | ULQ[b,c] | Max. Dilution |
|---|---|---|---|---|---|
| Tear Fluid | 5.11 | 0.1-1000 ng/mL | 12.5 ng/g | 12500000 ng/g | 100 |
| Bulbar Conjunctiva | 57.2 | 0.1-1000 ng/mL | 1.45 ng/g | 1450000 ng/g | 100 |
| Cornea | 68.0 | 0.1-1000 ng/mL | 1.22 ng/g | 12200 ng/g | 1 |

TABLE 4-3-continued

| Bioanalytical Range Summary | | | | | |
|---|---|---|---|---|---|
| Matrix | Ave. Tissue Weight (mg) | Assay Range of Standard Curve[a] | LLQ[b] | ULQ[b,c] | Max. Dilution |
| Aqueous Humor | NA | 0.1-1000 ng/mL | 0.100 ng/mL | 1000 ng/mL | 1 |
| Iris/Ciliary Body | 86.2 | 0.1-1000 ng/mL | 0.962 ng/g | 9620 ng/g | 1 |

Abbreviations:
LLQ—lower limit of quantitation
ULQ—upper limit of quantitation
NA—not applicable
[a]Nominal concentration (ng/ml) of analyte in 1:1 acetonitrile: water
[b]Approximate limits of quantitation based on average tissue weights.
[c]ULQ includes a maximum sample dilution factor used.

Discussion

With the exception of the tear fluid, exposure to LE was similar or greater in all ocular tissues examined following administration of the higher (0.75%) concentration unmodified LE formulation (Formulation 3) compared with Lotemax® Gel (Formulation 4). In most cases, the observed differences in exposure were less-than-proportional to dose (1.0- to 2.5-fold difference based on $C_{max}$ and $AUC_{(0-24h)}$) and not statistically significant.

When compared to Lotemax® Gel, exposure to LE following administration of the 0.38% micronized formulation (Formulation 2) was 1.2- to 4.3-fold lower in all ocular tissues examined, based on $C_{max}$ and $AUC_{(0-24h)}$. In the tear fluid and cornea, the differences in exposure were statistically significant.

Topical ocular administration of the lower concentration (0.38%) formulation prepared with submicron particles of LE (Formulation 1) provided significantly (p≤0.05) greater exposure to LE in the aqueous humor (1.9- to 2.5-fold), and similar or slightly greater exposure to LE in the iris/ciliary body (1.0- to 1.6-fold) and cornea (1.0 to 1.3-fold) compared with Lotemax® Gel (Formulation 4), based on $C_{max}$ and $AUC_{(0-24\ h)}$ values. Exposure to LE was lower in the tear fluid (1.4- to 1.9-fold) and significantly lower in the bulbar conjunctiva (1.4- to 2.8-fold), but these are not considered target tissues. In summary, based on $C_{max}$ and/or $AUC_{(0-24h)}$ values, exposure to LE was significantly greater in the aqueous humor, similar or greater in the iris/ciliary body and cornea, and lower in the tear fluid and bulbar conjunctiva following administration of the 0.38% submicron formulation (Formulation 1) compared to Lotemax® Gel. Despite the 24% reduction in administered dose, exposure to LE was statistically higher in the aqueous humor, a key target tissue, for the 0.38% submicron formulation (Formulation 1). This data indicates that the submicron particle size enhances drug penetration to key ocular tissues.

The fold differences for the formulations, as compared to Lotemax® Gel 0.5% LE, are summarized in Tables 4-4 to 4-6.

TABLE 4.4

| Fold Differences—Formulation 1 (0.38% LE Submicron) vs. Formulation 4 (0.5% Lotemax Gel) | | | | |
|---|---|---|---|---|
| | $C_{max}$ | $AUC_{(0-24\ h)}$ | $C_{max}$ Significant | AUC Significant |
| Tear Fluid | 0.70 | 0.54 | No | No |
| Bulbar Conjunctiva | 0.73 | 0.35 | No | Yes |

TABLE 4.4-continued

| Fold Differences—Formulation 1 (0.38% LE Submicron) vs. Formulation 4 (0.5% Lotemax Gel) | | | | |
|---|---|---|---|---|
| | $C_{max}$ | $AUC_{(0-24\ h)}$ | $C_{max}$ Significant | AUC Significant |
| Cornea | 1.26 | 1.04 | No | No |
| Aqueous Humor | 2.51 | 1.85 | Yes | Yes |
| Iris/Ciliary Body | 1.62 | 1.01 | No | No |

TABLE 4.5

| Fold Differences—Formulation 2 (0.38% LE Micronized) vs. Formulation 4 (0.5% Lotemax Gel) | | | | |
|---|---|---|---|---|
| | $C_{max}$ | $AUC_{(0-24\ h)}$ | $C_{max}$ Significant | AUC Significant |
| Tear Fluid | 0.23 | 0.33 | No | Yes |
| Bulbar Conjunctiva | 4.80 | 0.58 | No | No |
| Cornea | 0.85 | 0.54 | No | Yes |
| Aqueous Humor | 1.21 | 0.80 | No | No |
| Iris/Ciliary Body | 1.24 | 0.78 | No | No |

TABLE 4.6

| Fold Differences—Formulation 3 (0.75% LE Unmodified) vs. Formulation 4 (0.5% Lotemax Gel) | | | | |
|---|---|---|---|---|
| | $C_{max}$ | $AUC_{(0-24\ h)}$ | $C_{max}$ Significant | AUC Significant |
| Tear Fluid | 0.77 | 0.80 | No | No |
| Bulbar Conjunctiva | 1.37 | 1.02 | No | No |
| Cornea | 0.99 | 1.26 | No | No |
| Aqueous Humor | 1.70 | 1.24 | No | No |
| Iris/Ciliary Body | 2.50 | 1.28 | No | No |

Example 5—Investigation of the Effect of Particle Size and Concentration on the Ocular and Systemic Pharmacokinetics of 21-Desacetyl Difluprednate Following a Single Topical Ocular Administration of Difluprednate in a Gel Formulation to Dutch Belted Rabbits A total of 135 Dutch Belted rabbits were used in this pharmacokinetic study. On the day of dosing, animals received a single 35-µL topical ocular dose containing the appropriate formulation into each eye. Difluprednate (DFBA) is a prodrug and is rapidly hydrolyzed to 21-desacetyl DFBA after ocular instillation. The LC/MS/MS methods for the quantitation of 21-desacetyl DFBA in Dutch Belted rabbit ocular tissues and plasma were assessed for precision and accuracy, but were not fully validated or GLP-compliant. Overall, the performance of the analytical methods was deemed acceptable to support this nonclinical PK study.

Formulation 5-1—0.05% Submicron DFBA Gel Suspension—corresponding to Composition B with $D_{v50}$ of 0.2 µm and pH 6.1-6.2.

Formulation 5-2—0.2% Submicron DFBA Gel Suspension—Similar to Formulation 5-1 but containing 0.2% DFBA Formulation 5-3—0.8% Submicron DFBA Gel Suspension—Similar to Formulation 5-1 but containing 0.8% DFBA Formulation 5-4—0.8% Micronized DFBA Gel Suspension—Similar to Formulation 5-3 but containing 0.8% DFBA with $D_{v50}$ of 3 µm Formulation 5-5—DUREZOL® difluprednate ophthalmic emulsion, 0.05% DFBA, a sterile preserved ophthalmic emulsion FIGS. 36-42 report the concentrations of the DFBA metabolite, 21-desacetyl difluprednate, in various ocular tissues and plasma. Table 5.1 summarizes the effect of formulation and particle size of DFBA on the exposure of the metabolite in rabbit aqueous humor after single topical ocular administration of DFBA. Table 5.2 summarizes the effect of formulation and particle size of DFBA on the systemic exposure of 21-desacetyl DFBA in plasma after single topical ocular administration of DFBA.

TABLE 5.1

The effect of formulation and particle size on the exposure of 21-desacetyl DFBA in aqueous humor after a single topical ocular administration of DFBA to rabbits

| PK Parameter | Form. 5-5 | Form. 5-1 | Form. 5-2 | Form. 5-3 | Form. 5-4 |
|---|---|---|---|---|---|
| $C_{max}$ (ng/mL) | 60.3 | 185 | 314 | 350 | 377 |
| $T_{max}$ (h) | 0.5 | 0.5 | 0.5 | 1.0 | 0.5 |
| $AUC_{(0\text{-}last)}$ (ng · h/mL) | 143 | 425 | 603 | 830 | 880 |

TABLE 5.2

The effect of formulation and particle size on the systemic exposure of 21-desacetyl DFBA after a single topical ocular administration of DFBA to rabbits

| PK Parameter | Form. 5-5 | Form. 5-1 | Form. 5-2 | Form. 5-3 | Form. 5-4 |
|---|---|---|---|---|---|
| $C_{max}$ (ng/mL) | 1.4 | 4.57 | 8.21 | 10.9 | 4.25 |
| $T_{max}$ (h) | 0.25 | 0.25 | 0.25 | 0.5 | 0.25 |
| $AUC_{(0\text{-}last)}$ (ng · h/mL) | 0.761 | 8.67 | 18.7 | 21.7 | 11.3 |

The following observations were made from this study.

A single topical ocular administration of 0.05% DFBA with a submicron particle size gel suspension (Formulation 5-1) led to significantly greater concentrations and exposure of the active metabolite in all ocular tissues, compared to the 0.05% DFBA commercial emulsion product (Formulation 5-5). $C_{max}$ and AUC increased approximately 3-fold in aqueous humor.

The greatest concentration of DFBA metabolite concentration and exposure were found in the conjunctiva and cornea, followed by iris/ciliary body and aqueous humor.

Administering increasing concentrations of DFBA in a submicron gel formulation led to an increase in the exposure of the active metabolite in aqueous humor and other ocular tissues; however, this increase was not dose-proportional. There was no significant differences in $C_{max}$ in aqueous humor between submicron gel formulations at increasing concentrations.

There was no significant difference between submicron and micronized particles at 0.8% DFBA (Formulations 5-3 and 5-4) in any ocular tissues, except iris/ciliary body.

Systemic exposure of Formulation 5-1 was significantly greater after topical administration as compared to the Formulation 5-5. Systemic exposure also increased with increasing concentrations of DFBA (Formulations 5-2, 5-3 and 5-4).

Example 6—Stability Studies

Stability studies have shown that Composition A is storage-stable for a two-year shelf-life.

This invention has been described by reference to certain preferred embodiments; however, it should be understood that it may be embodied in other specific forms or variations thereof without departing from its special or essential characteristics. The embodiments described above are, therefore, considered to be illustrative in all respects and not restrictive, the scope of the invention being indicated by the appended claims rather than by the foregoing description.

What is claimed is:

1. An ophthalmic suspension comprising an ophthalmic active ingredient suspended in a formulation vehicle, wherein the ophthalmic active ingredient is present as milled particles that have $D_{v50}<1$ μm, and the formulation vehicle comprises a suspending agent comprising a carboxyvinyl polymer and a particle size stabilizing agent comprising a non-ionic cellulose derivative, wherein the non-ionic cellulose derivative is hydroxypropylmethyl cellulose, the carboxyvinyl polymer is polycarbophil, the ophthalmic active ingredient is loteprednol etabonate, and the suspension comprises loteprednol etabonate at about 0.38 wt %, polycarbophil at 0.1-0.5 wt %, and hydroxypropylmethyl cellulose at 0.1-0.5 wt %.

2. The suspension of claim 1, which is storage stable for at least one year.

3. The suspension of claim 1, which is storage stable for at least two years.

4. The suspension of claim 1, wherein the loteprednol etabonate is present as particles that have $D_{v90}<5$ μm.

5. The suspension of claim 1, wherein the non-ionic cellulose derivative is hydroxypropylmethyl cellulose E3LV and is present at a concentration of at least 0.25%.

6. The suspension of claim 1, wherein the non-ionic cellulose derivative is hydroxypropylmethyl cellulose E4M.

7. The suspension of claim 1, wherein the poloxamer nonionic surfactant comprises poloxamer 407.

8. The suspension of claim 1, comprising hydroxypropylmethyl cellulose E3LV or hydroxypropylmethyl cellulose E4M, present at 0.15-0.25 wt %.

9. The suspension of claim 1, comprising hydroxypropylmethyl cellulose E4M at 0.15-0.25 wt %.

10. The suspension of claim 1, wherein the loteprednol etabonate is present as particles having $D_{v90}<3$ μm.

11. The suspension of claim 1, wherein the loteprednol etabonate is present as particles having $D_{v90}<3$ μm and $D_{v50}<0.6$ μm.

12. The ophthalmic suspension of claim 1, wherein upon storage of the suspension at 40° C. for 8.5 months, the particles will subsequently have a volume mean diameter of less than or equal to 1.23 micrometers measured using light diffraction.

13. The ophthalmic suspension of claim 1, wherein the suspension further comprises benzalkonium chloride at 0.001-0.01 wt %, edetate disodium dihydrate at 0.01-0.1 wt %, sodium chloride at 0.01-0.1 wt %, poloxamer nonionic surfactant at 0.1-1.0 wt %, and glycerin and propylene glycol at 0.1-2 wt %.

14. The ophthalmic suspension of claim 13, wherein the suspension further comprises a borate buffer at 0.01-1 wt %.

15. A method of treating an ophthalmic inflammatory condition comprising administering to an eye of a patient in need of said treating a suspension comprising an ophthalmic anti-inflammatory active ingredient suspended in a formulation vehicle, wherein the ophthalmic anti-inflammatory active ingredient is present as milled particles that have $D_{v50}<1$ μm, and the formulation vehicle comprises a suspending agent comprising a carboxyvinyl polymer and a particle size stabilizing agent comprising a non-ionic cellulose derivative, wherein the non-ionic cellulose derivative is hydroxypropylmethyl cellulose, the carboxyvinyl polymer is polycarbophil, the ophthalmic active ingredient is loteprednol etabonate, and the suspension comprises loteprednol etabonate at about 0.38 wt %, polycarbophil at 0.1-0.5 wt %, and hydroxypropylmethyl cellulose at 0.1-0.5 wt %.

16. The method of claim 15, wherein the loteprednol etabonate is present as particles that have $D_{v90}<5$ μm and $D_{v50}<1$ μm.

17. The method of claim 15, wherein the suspension further comprises benzalkonium chloride at 0.001-0.01 wt %, edetate disodium dihydrate at 0.01-0.1 wt %, sodium chloride at 0.01-0.1 wt %, poloxamer nonionic surfactant at 0.1-1.0 wt %, and glycerin and propylene glycol at 0.1-2 wt %.

18. The method of claim 17, wherein the suspension further comprises a borate buffer at 0.01-1 wt %.

19. The method of claim 15, wherein the suspension comprises hydroxypropylmethyl cellulose E3LV or hydroxypropylmethyl cellulose E4M, present at 0.15-0.25 wt %.

20. The method of claim 15, wherein the suspension comprises hydroxypropylmethyl cellulose E4M at 0.15-0.25 wt %.

* * * * *